(12) United States Patent
Burns et al.

(10) Patent No.: US 6,306,873 B1
(45) Date of Patent: Oct. 23, 2001

(54) SUBSTITUTED β-THIOCARBOXYLIC ACIDS

(75) Inventors: Christopher J. Burns, Rosemont; Richard Labaudiniere, Collegeville; Stephen Condon, Chester Springs; Robert D. Groneberg, Collegeville; Rose M. Mathew, Phoenixville; Joseph M. Salvino, Schwenksville, all of PA (US)

(73) Assignee: Aventis Pharmaceuticals Products Inc., Bridgewater, NJ (US)

( * ) Notice: Subject to any disclaimer, the term of this patent is extended or adjusted under 35 U.S.C. 154(b) by 0 days.

(21) Appl. No.: 09/357,734

(22) Filed: Jul. 20, 1999

Related U.S. Application Data

(63) Continuation of application No. PCT/IB98/00082, filed on Jan. 21, 1998.
(60) Provisional application No. 60/041,962, filed on Apr. 3, 1997.

(30) Foreign Application Priority Data

Jan. 22, 1997 (GB) .................................................. 9701264

(51) Int. Cl.[7] ...................... C07D 209/48; C07D 215/06; C07D 333/24; C07D 317/60; C07C 323/62; C07C 317/44; C07C 317/46; C07C 317/50; A61K 31/16
(52) U.S. Cl. ............................. 514/299; 560/13; 560/17; 560/32; 560/33; 562/429; 562/431; 562/621; 514/340; 514/347; 514/357; 514/364; 514/394; 514/418; 514/423; 514/424; 514/438; 514/464; 514/506; 514/530; 514/562; 514/563; 514/570; 546/166; 546/269.4; 546/294; 546/337; 548/131; 548/309.7; 548/477; 548/531; 548/556; 549/77; 549/441
(58) Field of Search ................................ 546/166, 269.4, 546/294, 337; 548/131, 309.7, 477, 531, 556; 549/77, 441; 560/13, 17, 32, 33; 562/429, 431, 621; 514/299, 340, 347, 357, 364, 394, 418, 423, 424, 438, 464, 506, 530, 562, 563, 570, 575

(56) References Cited

FOREIGN PATENT DOCUMENTS

| | | |
|---|---|---|
| 0497564A | 8/1992 | (EP) . |
| 0606046A1 | 7/1994 | (EP) . |
| 0780386A | 6/1997 | (EP) . |
| 2 661 676 A | 11/1991 | (FR) . |
| 7-196598 | 8/1995 | (JP) . |
| WO94 10990A | 5/1994 | (WO) . |
| WO9504045A | 2/1995 | (WO) . |
| WO9805635A | 2/1998 | (WO) . |
| WO98/13340 | 4/1998 | (WO) . |

OTHER PUBLICATIONS

Database Caplus on STN, Acc. No. 1977:528062, Poplawski et al., 'Studies of the bacteriostatic effects of some sulfur derivatives of naphthalene and benzene on selected bacterial strains and Candida albicans.' Przegl. Lek, (1977), 34(4), pp. 449–452 (abstract).*
International Preliminary Examination Report for PCT/IB98/00082.

* cited by examiner

Primary Examiner—Johann Richter
Assistant Examiner—Brian J. Davis
(74) Attorney, Agent, or Firm—Irving Newman

(57) ABSTRACT

This invention relates to compounds of general formula (I):

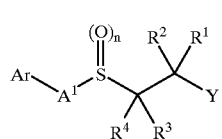

(I)

in which Ar is a group selected from:

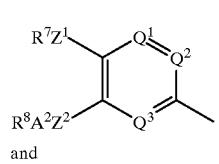

(i)

and

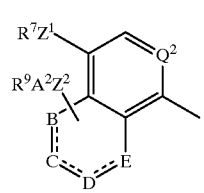

(ii)

A1, A2, B, C, D, E, Q1–Q3, R1–R9, Z1 and Z2 are as defined in the disclosure, and Y represents carboxy or an acid bioisostere. These compounds inhibit the production or physiological effects of TNF and inhibit cyclic AMP phosphodiesterase. The invention is also directed to pharmaceutical compositions comprising compounds of formula (I), their pharmaceutical use and methods for their preparation.

30 Claims, No Drawings

SUBSTITUTED β-THIOCARBOXYLIC ACIDS

CROSS REFERENCE TO RELATED APPLICATIONS

This application is acontinuation application of International Application No. PCT/IB98/00082, filed Jan. 21, 1998 and claims benefit of Prov. No. 60/041,962 filed Apr. 3, 1997.

This invention is directed to substituted, thiocarboxylic acids and their bioisosteres, their preparation, pharmaceutical compositions containing these compounds, and their pharmaceutical use in the treatment of disease states associated with proteins that mediate cellular activity. This invention is also directed to intermediates useful in preparing the substituted, thiocarboxylic acids and their bioisosteres.

Tumour necrosis factor (TNF) is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, fibroblasts and endothelial cells to release tissue damaging mediators. TNF also activates monocytes, macrophages and T-lymphocytes to cause the production of colony stimulating factors and other pro-inflammatory cytokines such $IL_1$, $IL_6$, $IL_8$ and GM-CSF, which in some case mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

The discussion herein relates to disease states associated with TNF including those disease states related to the production of TNF itself, and disease states associated with other cytokines, such as but not limited to $IL_1$, or $IL_6$, that are modulated by associated with TNF. For example, a $IL_1$ associated disease state, where $IL_1$ production or action is exacerbated or secreted in response to TNF, would therefore be considered a disease state associated with TNF. TNF-alpha and TNF-beta are also herein referred to ccollectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

Cyclic AMP phosphodiesterases are important enzymes which regulate cyclic AMP levels and in turn thereby regulate other important biological reactions. The ability to regulate cyclic AMP phosphodiesterases therefore, has been implicated as being capable of treating assorted biological conditions. In particular, inhibitors of type IV cyclic AMP phosphodiesterase have been implicated as being bronchodilators agents, prophylactic agents useful against asthma and as agents for inhibiting eosinophil accumulation and of the function of eosinophils, and for treating other diseases and conditions characterized by, or having an etiology involving, morbid eosinophil accumulation. Inhibitors of cyclic AMP phosphodiesterase are also implicated in treating inflammatory diseases, proliferative skin diseases and conditions associated with cerebral metabolic inhibition.

We have now found a novel group of compounds which have valuable pharmaceutical properties, in particular the ability to regulate proteins that mediate cellular activity, for example, cyclic AMP phosphodiesterases (in particular type IV) and/or TNF. Compounds structurally similar to those of the present invention have been described in EP 0 780 386 and WO 97/24117 as inhibitors of matrix metalloproteinases. We have surprisingly found that the compounds of the present invention inhibit AMP phosphodiesterases (in particular type IV) and/or TNF without concomitant activity against matrix metalloproteinases.

Thus, in one aspect, the present invention is directed to compounds of general formula (I):

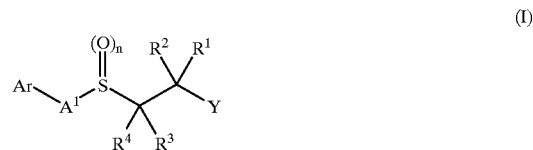

wherein $R^1$ and $R^3$ may be the same or different and each independently represents a group —$L^1$—$R^5$ [where $L^1$ is a direct bond, a straight or branched $C_{1-6}$alkylene chain, a straight or branched $C_{2-6}$alkenylene chain, a straight or branched $C_{2-6}$alkynylene chain or a straight or branched $C_{1-6}$alkylene chain containing an oxygen or sulfur atom, a phenylene, imino (—NH—) or alkylimino linkage, or a sulfinyl or sulfonyl group, in which each of the alkylene, alkenylene and alkynylene chains may be optionally substituted, the substituents chosen from alkoxy, aryl, carboxy, cyano, cycloalkyl, halogen, heteroaryl, hydroxyl, or oxo; and $R^5$ represents hydrogen, aryl, aroyl, carboxy or an acid bioisostere, cyano, cycloalkyl, cycloalkenyl, heterocycloalkyl, heteroaryl, arylalkoxycarbonyl, —NH—C(=O)—$NH_2$, —C=N—O—C(=O)—$NH_2$, —C(=O)—$NY^1Y^2$, (where $Y^1$ and $Y^2$ are independently hydrogen, alkyl, arylalkyl, and aryl, or the group $NY^1Y^2$ may form a 4-6 membered cyclic amine {which may optionally contain a further heteroatom selected from O, S, or $NR^6$ in which $R^6$ is hydrogen, alkyl, aryl or arylalkyl, or which may be fused to an additional aromatic ring}), —$NY^1SO_2$aryl, —$NHR^6$, —$SR^6$, or —$OR^6$];

$R^2$ and $R^4$ may be the same or different and are each independently hydrogen or alkyl; or $R^2$ and $R^4$ together form a bond; or $R^1$ and $R^2$, or $R^1$ and $R^3$, or $R^3$ and $R^4$ together with the carbon atom(s) to which they are attached form a 3 to 8 membered cycloalkyl or cycloalkenyl ring, optionally substituted by alkyl, arylalkyl, or heteroarylalkyl, and which may optionally contain a heteroatom selected from O, S or $NR^6$; or $R^1$ and $R^3$ together with the carbon atoms to which they are attached form a heteroaryl ring;

Y represents carboxy or an acid bioisostere;

$A^1$ represents a direct bond, a straight or branched $C_{1-4}$alkylene chain or a $NR^6$ group; and Ar is a group chosen from

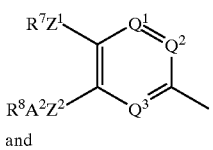

(i)

and

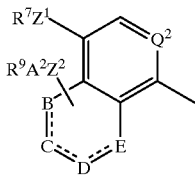

(ii)

where the dotted lines indicate optional bonds between B-C, and /or C-D, and/or D-E;

$R^7$ represents a straight- or branched-chain alkyl group of 1 to about 6 carbon atoms, optionally substituted by one or more halogen atoms, or when $Z^1$ represents a direct bond $R^7$ may also represent a hydrogen atom or a lower alkenyl or lower alkynyl group;

$R^8$ represents an optionally substituted cycloalkyl, cycloalkenyl, heterocycloalkyl, aryl, heteroaryl or partially saturated bicycloaryl group;

$R^9$ represents $R^{10}$, $-OR^{10}$, $-SR^{10}$, $-SOR^{12}$, $-SO_2R^{12}$, $-SO_2NR^{10}R^{11}$, $-NR^{10}SO_2R^{12}$, $-NR^{10}R^{11}$, $-O(C=O)NR^{10}R^{11}$, $NR^{10}C(=O)R^{12}$, $-N(OH)C(=O)R^{12}$, or $-C(=O)N(OH)R^{12}$ (where $R^{10}$ and $R^{11}$, which may be the same or different, each represent a hydrogen atom, or an alkyl, alkenyl, heterocycloalkyl, cycloalkyl, cycloalkenyl, aryl, heteroaryl, arylalkyl or heteroarylalkyl group, or the group $NR^{10}R^{12}$ may also represents a 3 to 7 membered cyclic amine optionally containing one or more additional heteroatom selected from O, $NR^6$, or S, and $R^{12}$ represents an alkyl, alkenyl, heterocycloalkyl, cycloalkyl, cycloalkenyl, aryl, heteroaryl, arylalkyl or heteroarylalkyl group);

$A^2$ represents a direct bond, a straight- or branched $C_{1-6}$alkylene chain optionally substituted by halogen, hydroxyl, alkoxy, oxo, cycloalkyl, aryl or heteroaryl; or $A^2$ represents a straight- or branched-carbon chain comprising from 2 to about 6 carbon atoms which contains a double or triple carbon-carbon bond, or is interrupted by an oxygen or sulfur atom, a phenylene, imino (—NH—) or alkylimino linkage, or a sulfinyl or sulfonyl group;

$Z^1$ represents an oxygen or sulfur atom, a direct bond or NH;

$Z^2$ represents an oxygen or sulfur atom, or a direct bond;

B, C, D, and E independently represent a carbon atom or a heteroatom selected from O, S, $NOR^{13}$ or $NR^{13}$ (where $R^{13}$ is hydrogen or a $C_{1-4}$ straight- or branched-chain alkyl, aryl, aryl$C_{1-4}$alkyl, heteroaryl or heteroaryl$C_{1-4}$alkyl group), or three of B, C, D or E represent a carbon atom or a heteroatom as defined above and the other represents a direct bond; but excluding compounds where two O or S atoms are in adjacent positions;

$Q^1$, $Q^2$ and $Q^3$, which may be the same or different, each represents a CH or $CX^1$ linkage or a nitrogen atom (where $X^1$ represents a halogen atom); and n is 0, 1 or 2, (with the proviso that when $A^1$ is $NR^6$ n is 2);

and N-oxides thereof, and their prodrugs, pharmaceutically acceptable salts, and solvates (e.g. hydrates), thereof.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993, 33,p576–579 "Application Of Bioisosterism To New Drug Design"; Zhao, Huaxue Tongbao, 1995,p34–38 "Bioisosteric Replacement And Development Of Lead Compounds In Drug Design"; Graham, Theochem, 1995,343,p105–109 "Theoretical Studies Applied To Drug Design:ab initio Electronic Distributions In Bioisosteres"). Examples of suitable acid bioisosteres include:

—C(=O)—NHOH, —C(=O)—CH$_2$OH, —C(=O)—CH$_2$SH, —C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as defined herein. Preferred acyls contain a lower alkyl group. Exemplary acyl groups include formyl, acetyl, propanoyl, 2-methylpropanoyl, butanoyl and palmitoyl.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more of halo or cycloalkyl. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group in which the alkyl group is as defined herein. Exemplary alkoxy groups include methoxy, ethoxy, n-propoxy, i-propoxy, n-butoxy and heptoxy.

"Alkoxyalkyl" means an alkyl-O-alkyl— group in which the alkyl groups are independently as defined herein. Exemplary alkoxy groups include methoxyethyl, ethoxymethyl, n-butoxymethyl and cyclopentylmethyloxyethyl.

"Alkoxycarbonyl" means an alkyl-O-CO— group in which the alkyl group is as defined herein. Exemplary alkoxycarbonyl groups include methoxy- and ethoxycarbonyl.

"Alkyl" means an aliphatic hydrocarbon group which may be straight or branched having about 1 to about 15 carbon atoms in the chain. Preferred alkyl groups have 1 to about 12 carbon atoms (e.g. 1 to 6 carbon atoms) in the chain. Branched means that one or more lower alkyl groups such as methyl, ethyl or propyl are attached to a linear alkyl chain. "Lower alkyl" means an alkyl group comprising about 1 to about 4 carbon atoms in a chain which may be straight or branched. The alkyl group may be substituted by one or more of halo, cycloalkyl or cycloalkenyl. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl. Preferred alkyl groups for $R^7$ include methyl, fluoromethyl, difluoromethyl, trifluoromethyl, and ethyl.

"Alkylenedioxy" means an -O-alkyl-O— group in which the alkyl group is as defined above. Exemplary alkylenedioxy groups include methylenedioxy and ethylenedioxy.

"Alkylsulfinyl" means an alkyl-SO— group in which the alkyl group is as defined above. Preferred groups are those in which the alkyl group is lower alkyl.

"Alkylsulfonyl" means an alkyl-SO2— group in which the alkyl group is as defined above. Preferred groups are those in which the alkyl group is lower alkyl.

"Alkylthio" means an alkyl-S— group in which the alkyl group is as previously described. Exemplary alkylthio groups include methylthio, ethylthio, i-propylthio and heptylthio. "Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. Exemplary alkynyl groups include ethynyl, propynyl, n-butynyl, i-butynyl, 3-methylbut-2-ynyl, and n-pentynyl. "Aroyl" means an aryl-CO— group in which the aryl group is as defined herein. Exemplary groups include benzoyl and 1- and 2-naphthoyl.

37 Aroylamino" is an aroyl-NH— group wherein aroyl is as defined herein. "Aryl" as a group or part of a group denotes an optionally substituted monocyclic or multicyclic aromatic carbocyclic moiety of about 6 to about 10 carbon atoms. Exemplary aryl include phenyl or naphthyl, or phenyl or naphthyl substituted with one or more aryl group substituents which may be the same or different, where "aryl group substituent" includes acyl, acylamino, alkoxy, alkoxycarbonyl, alkyl, alkylenedioxy, alkylsulfinyl, alkylsulfonyl, alkylthio, aroyl, aroylamino, aryl, arylalkoxy, arylalkoxycarbonyl, arylalkyl, arylalkylthio, aryloxy, aryloxycarbonyl, arylsulfinyl, arylsulfonyl, arylthio, carboxy, cyano, halo, heteroaroyl, heteroaryl, heteroarylalkyl, heteroarylamino, heteroaryloxy, hydrogen, hydroxy, hydroxyalkyl, nitro, $Y^3Y^4N$—, $Y^3Y^4NCO$— or $Y^3Y^4NSO_2$—, where $Y^3$ and $Y^4$ are independently hydrogen, alkyl, arylalkyl, and aryl, or the substituent $Y^3Y^4N$— forms a 4–6 membered cyclic amine which optionally contains an additional heteroatom selected from O, S or $NR^6$. Preferred aryl group substituents include acyl, acylamino, alkoxycarbonyl, alkyl, alkylthio, aroyl, cyano, halo, hydrogen, hydroxy, nitro, $Y^3Y^4N$—, $Y^3Y^4NCO$— or $Y^3Y^4NSO_2$—, where $Y^3$ and $Y^4$ are independently hydrogen and alkyl.

"Arylalkenyl" means an aryl-alkenyl— group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl— group in which the aryl and alkyl are as previously described. Preferred arylalkyls contain a lower alkyl moiety. Exemplary arylalkyl groups include benzyl, 2-phenethyl and naphthlenemethyl.

"Arylalkyloxy" means an arylalkyl-O— group in which the arylalkyl group is as previously described. Exemplary arylalkyloxy groups include benzyloxy and 1- or 2-naphthalenemethoxy.

"Arylalkyloxyalkenyl" means an arylalkyl-O-alkenyl group in which the arylalkyl and alkenyl groups are as previously described. An exemplary arylalkyloxyalkenyl group is 3-benzyloxyallyl.

"Arylalkyloxyalkyl" means an arylalkyl-O-alkyl group in which the arylalkyl and alkyl groups are as previously described. An exemplary arylalkyloxyalkyl group is benzyloxyethyl.

"Arylalkoxycarbonyl" means an arylalkyl-O-CO— group. An exemplary arylalkoxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl- group in which the aryl and alkynyl are as previously described. Preferred arylalkynyls contain a lower alkynyl moiety. An exemplary arylalkynyl group is phenylacetylenyl.

"Aryloxy" means an aryl-O— group in which the aryl group is as previously described. Exemplary aryloxy groups include phenoxy and naphthoxy.

"Aryloxyalkenyl" means an aryl-O-alkenyl— group in which the aryl or alkenyl groups are as previously described. An exemplary aryloxyalkenyl groups is phenoxyallyl.

"Aryloxyalkyl" means an aryl-O-alkyl— group in which the aryl or alkyl groups are as previously described. An exemplary aryloxyalkyl groups is phenoxypropyl.

"Aryloxycarbonyl" means an aryl-O-CO— group in which the aryl group is as previously described. Exemplary aryloxycarbonyl groups include phenoxy- and naphthoxycarbonyl. "Arylsulfinyl" means an aryl-SO— group in which the aryl group is as previously described. "Arylsulfonyl" means an aryl-SO$_2$— group in which the aryl group is as previously described.

"Arylthio" means an aryl-S— group in which the aryl group is as previously described. Exemplary arylthio groups include phenylthio and naphthylthio.

"Cycloalkenyl" means a non-aromatic monocyclic or multicyclic ring system containing a carbon-carbon double bond and having about 3 to about 10 carbon atoms. Preferred monocyclic cycloalkenyl rings include cyclopentenyl, cyclohexenyl or cycloheptenyl; more preferred is cyclopentenyl. A preferred multicyclic cycloalkenyl ring is norbornenyl. The cycloalkenyl group may be substituted by one or more halo, methylene ($H_2C=$) or alkyl.

"Cycloalkyl" means a non-aromatic mono- or multicyclic ring system of about 3 to about 10 carbon atoms. Exemplary monocyclic cycloalkyl rings include cyclopropyl, cyclopentyl, cyclohexyl and cycloheptyl. Preferred monocyclic cycloalkyl rings for $R^8$ include cyclopentyl and cyclohexyl. A preferred monocyclic cycloalkyl rings for $R^9$ is cyclopropyl. Exemplary multicyclic cycloalkyl rings include perhydronaphthyl, adamant-(1- or 2-)yl and norbornyl and spirobicyclic groups, e.g. spiro[4,4]non-2-yl. The cycloalkyl group may be substituted by one or more (e.g. 1, 2 or 3) substituents chosen from halo, $R^{12}$, $OR^{10}$, $SR^{12}$, $SOR^{12}$, $SO_2R^{12}$, $NR^{10}R^{11}$, $=NOR^{10}$, $=NNHR^{12}$, $=NOCONHR^{12}$, $=NCO_2R^{12}$, $NHCOR^{12}$, $NHSO_2R^{12}$, $SO_2NR^{10}R^{11}$, $CONH(CH_2)_nCO_2R^6$, $CONR^{10}R^{11}$, $N_3$, oxo, cyano, or $CO_2R^6$.

"Cycloalkyoxy" means an cycloalkyl-O— group in which the cycloalkyl group is as previously described. Exemplary cycloalkoxy groups include cyclopentyloxy and cyclohexyloxy.

"Halo" means fluoro, chloro, bromo, or iodo. Preferred are fluoro, chloro or bromo, and more preferred are fluoro or chloro.

"Heteroaroyl" means a heteroaryl-CO— group in which the heteroaryl group is as defined herein. An exemplary heteroaroyl group is pyridylcarbonyl.

"Heteroaryl" as a group or part of a group denotes an optionally substituted aromatic monocyclic or multicyclic hydrocarbon ring system of about 5 to about 10 atoms in which one or more of the ring members is/are element(s) other than carbon, for example nitrogen, oxygen or sulphur. The "heteroaryl" may also be substituted by one or more aryl group substituents. Examples of suitable optionally substituted heteroaryl groups include furyl, isoxazolyl, isoquinolinyl, isothiazolyl, 1,2,3-oxadiazole, 1,2,4-oxadiazole, 1,2,5-oxadiazole, 1,3,4-oxadiazole, pyrazolyl, pyrazinyl, pyridazinyl, pyridyl, pyrimidinyl, quinolinyl, 1,3,4-thiadiazolyl, thiazolyl, thienyl, and 1,2,3- and 1,2,4-triazolyl groups, optionally substituted by one or more aryl group substituents as defined above. When $R^8$ or $R^9$ contains an optionally substituted heteroaryl group this may particularly represent an optionally substituted "azaheteroaryl" group (where the term "azaheteroaryl" means a heteroaryl group of about 5 to about 10 ring members in which one or more of the ring members is/are nitrogen). Optional substituents for the heteroaryl group within $R^8$ or $R^9$ include, for example, halogen atoms and alkyl, aryl, arylalkyl, hydroxy, oxo, hydroxyalkyl, haloalkyl (for example trifluoromethyl), alkoxy, haloalkoxy (for example trifluoromethoxy), aryloxy, and arylalkyloxy groups. Preferred heteroaryl groups within $R^8$ include optionally substituted thienyl, thiazolyl, pyridyl, 1,2,4-oxadiazole or 1,3,4-oxadiazole. A preferred heteroaryl groups within $R^9$ is optionally substituted pyridyl.

"Heteroarylalkenyl" means an heteroaryl-alkenyl- group in which the heteroaryl and alkenyl are as previously described. Preferred heteroarylalkenyls contain a lower alkenyl moiety. An exemplary heteroarylalkenyl group is 4-pyridylvinyl.

"Heteroarylalkyl" means an heteroaryl-alkyl- group in which the heteroaryl and alkyl are as previously described. Preferred heteroarylalkyls contain a lower alkyl moiety. An exemplary heteroarylalkyl group is 4-pyridylmethyl.

"Heteroarylalkyloxy" means an heteroarylalkyl-O— group in which the heteroarylalkyl group is as previously described. An exemplary heteroarylalkyloxy group is 4-pyridylmethyloxy.

"Heteroarylalkyloxyalkenyl" means an heteroarylalkyl-O-alkenyl group in which the heteroarylalkyl and alkenyl groups are as previously described. An exemplary heteroarylalkyloxyalkenyl group is 4-pyridylmethyloxyallyl.

"Heteroarylalkyloxyalkyl" means an heteroarylalkyl-O-alkyl group in which the heteroarylalkyl and alkyl groups are as previously described. An exemplary heteroarylalkyloxy group is 4-pyridylmethyloxyethyl.

"Heteroarylalkynyl" means an heteroaryl-alkynyl- group in which the heteroaryl and alkynyl are as previously described. Preferred heteroarylalkynyls contain a lower alkynyl moiety. An exemplary heteroarylalkynyl group is 4-pyridylethynyl.

"Heterocycloalkyl" means an about 4 to about 10 member monocyclic or multicyclic ring system wherein one or more of the atoms in the ring system is an element other than carbon chosen amongst nitrogen, oxygen or sulfur. Exemplary heterocycloalkyl moieties include pyrrolidinyl, piperidinyl, morpholinyl, piperazinyl, quinuclidinyl, tetrahydropyranyl, tetrahydrothiophenyl, tetrahydrofuranyl, oxazolidinyl, imidazolidinyl or tetrahydropyrimidinyl. The heterocycloalkyl may be optionally substituted by one or more substituents, on one or more (e.g. 1, 2 or 3) of the ring carbon atoms, and the substituents are chosen from $R^{12}$, oxo, cyano, $CO_2R^{10}$, $CONHCH_2CO_2R^{10}$, or hydroxyalkyl. In addition to the aforementioned substitution heterocycloalkyls containing one or more nitrogen atoms may be substituted on a ring nitrogen atom and the substituent is chosen from alkyl, cycloalkyl, aryl, arylalkyl, heteroaryl, heteroarylalkyl, $(CH_2)_nCO_2R^{10}$, $(CH_2)_nCONR^{10}R^{11}$, $(CH_2)COR^{12}$, $COR^{12}$, $SO_2R^{12}$, or $OR^{12}$.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Partially saturated bicycloaryl" means a group in which an aryl and a cycloalkyl group are fused together to form a bicyclic structure. Exemplary arylalkyl groups include indanyl and tetrahydronaphthyl, especially indanyl.

"Prodrug" means a compound which is convertible in vivo by metabolic means (e.g. by hydrolysis) to a compound of formula (I), including N-oxides thereof, for example an ester of a compound of formula (I).

Suitable esters are of many different types, for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

An especially useful class of esters may be formed from acid moieties selected from those described by Bundgaard et. al., J. Med. Chem., 32, No. 12, (1989), 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be apparent to those skilled in the art that certain compounds of the invention can exhibit isomerism, for example optical isomerism and geometrical isomerism. All such isomers of the compounds of the invention, and their mixtures, are within the scope of the invention.

With reference to formula (I) above, the following are particular and preferred groupings:

$R^1$ may particularly represent a group —$L^1$—$R^5$ where $L^1$ represents a direct bond and $R^5$ is hydrogen.

$R^1$ may also particularly represent a group —$L^1$—$R^5$ where $L^1$ represents a direct bond and $R^5$ is $NHR^6$, especially $NH_2$.

$R^1$ may also particularly represent a group —$L^1$—$R^5$ where $L^1$ represents a direct bond and $R^5$ is $OR^6$, especially OH.

$R^1$ may also particularly represent a group —$L^1$—$R^5$ where $L^1$ represents a straight or branched $C_{1-6}$alkylene chain, especially ethylene, and $R^5$ is $SR^6$, especially thiophenyl.

$R^1$ may also particularly represent a group —$L^1$—$R^5$ where $L^1$ represents a straight or branched $C_{1-6}$alkylene chain, preferably methylene, and $R^5$ is hydrogen.

$R^1$ preferably represents a hydrogen atom.

$R^2$ preferably represents hydrogen, or alkyl (e.g. methyl) and is more preferably hydrogen.

When $R^1$ and $R^2$ together with the carbon atom to which they are attached form a cycloalkyl ring, they preferably form a cyclopentyl ring.

$R^3$ particularly represents a group —$L^1$—$R^5$ where $L^1$ represents a straight or branched $C_{1-6}$alkylene chain, especially methylene, ethylene, trimethylene, tetramethylene, more preferably tetramethylene, and $R^5$ is hydrogen.

$R^3$ may also particularly represent a group —$L^1$—$R^5$ where $L^1$ represents a straight or branched $C_{1-6}$alkylene chain, especially methylene, ethylene, trimethylene, tetramethylene, more preferably tetramethylene, and $R^5$ is aryl especially phenyl.

$R^3$ may also particularly represent a group —$L^1$—$R^5$ where $L^1$ represents a straight or branched $C_{1-6}$alkylene chain, especially methylene, ethylene, trimethylene, tetramethylene, more preferably tetramethylene, and $R^5$ is heteroaryl.

$R^3$ may also particularly represent a group —$L^1$—$R^5$ where $L^1$ represents a straight or branched $C_{1-6}$alkylene chain, especially ethylene or trimethylene, and $R^5$ is —C(=O)—$NY^1Y^2$ where $Y^1$ and $Y^2$ are as hereinbefore defined, for example —C(=O)—NMePh or 3,4-dihydro-2H-quinolin-1-ylcarbonyl.

$R^3$ may also particularly represent a group —$L^1$—$R^5$ where $L^1$ represents a straight or branched $C_{1-6}$alkylene chain, which contains an alkylimino linkage, especially methylimino, and $R^5$ is an arylalkyl ester of a carboxy group (e.g. benzyloxycarbonyl).

$R^3$ may also particularly represent a group —$L^1$—$R^5$ where $L^1$ represents a straight or branched $C_{1-6}$alkylene chain, which contains an oxygen atom, especially ethyloxy, and $R^5$ is —C(=O)$NY^1Y^2$ where $Y^1$ and $Y^2$ are as hereinbefore defined, for example —C(=O)NMePh.

$R^3$ may also particularly represent a group —$L^1$—$R^5$ where $L^1$ represents a straight or branched $C_{1-6}$alkylene chain, especially trimethylene, and $R^5$ is heterocycloalkyl, for example N-phthalimidyl.

$R^3$ may also particularly represent a group —$L^1$—$R^5$ where $L^1$ represents a direct bond and $R^5$ is aryloxyaryl such as methoxyphenoxyphenyl especially 3-(4-methoxyphenoxy)phenyl.

$R^3$ may also particularly represent a group —$L^1$—$R^5$ where $L^1$ represents a direct bond and $R^5$ is aryl or heteroaryl for example phenyl or thienyl.

$R^3$ may also particularly represent a group —$L^1$—$R^5$ where $L^1$ represents a direct bond and $R^5$ is aryl- or heteroaryl-alkyloxyaryl such as benzyloxyphenyl (especially 4-benzyloxyphenyl).

$R^4$ preferably represents hydrogen or alkyl (e.g. methyl), and is more preferably hydrogen.

Y may particularly represent carboxy or more preferably a —C(=O)NHOH group.

$A^1$ preferably represents a direct bond.

Ar may particularly represents a group (i) where:

$R^8$ particularly represents:

(i) a $C_{3-8}$cycloalkyl group (for example cyclopropyl, cyclopentyl, cyclohexyl or cycloheptyl) optionally substituted by:
halo, preferably fluoro;
hydroxy;
alkoxy;

an aryl group, for example phenyl;
an arylC$_{1-4}$alkyl group, for example benzyl;
an aryloxy group, for example phenoxy;
an arylC$_{1-4}$alkyloxy group, for example benzyloxy;
a heteroaryl group, for example pyridyl;
or a heteroaryloxy group, for example pyridyloxy; or (ii) a C$_{3-7}$cycloalkyl group containing a nitrogen atom (for example pyrrolidinyl or piperidinyl) which is optionally substituted by:
an aryl group, for example phenyl;
an arylC$_{1-4}$alkyl group, for example benzyl or phenethyl;
a C$_{1-6}$alkoxycarbonyl group, for example t-butyloxycarbonyl;
or an aroyl group, for example benzoyl; or (iii) an optionally substituted heteroaryl group, preferably optionally substituted thienyl, thiazolyl, pyridyl, oxidopyridinio, 1,2,4-oxadiazolyl, 1,3,4-oxadiazolyl; or (iv) an optionally substituted aryl group, such as a phenyl or alkoxyphenyl, or preferably a 4-methoxyphenyl, group; or (v) a partially saturated bicycloaryl group particularly a cyclopentyl moiety fused to an aryl ring, for example indanyl, especially a 2-indanyl group; or (vi) a R$^a$R$^b$N- group, such as a piperidinyl, morpholinyl or pyrrolidinyl, especially 2-oxo-pyrrolidinyl; substituted 1,2,4-oxadiazolyl or 1,3,4-oxadiazolyl particularly where the substituent is an optionally substituted phenyl group or a heteroaryl (e.g. pyridyl) group; or (vii) a substituted 1,2,4-oxadiazol-5-yl or 1,3,4-oxadiazol-5-yl group each substituted in the 3- and 2-positions respectively by an optionally substituted phenyl group (e.g. 4-halophenyl or 4-alkoxyphenyl) or more especially substituted in the 3- and 2-positions respectively by a heteroaryl (e.g. pyridyl such as 2-pyridyl) group;

A$^2$ particularly represents a direct bond, an unsubstituted straight C$_{1-4}$alkylene chain alkylene linkage containing from 1 to 4 carbon atoms, i.e. a methylene, ethylene, trimethylene or tetramethylene linkage, or a straight chain C$_{2-3}$alkylene linkage containing an oxygen atom especially a —CH$_2$OCH$_2$CH$_2$— or —OCH$_2$CH$_2$— linkage; and Q$^1$, Q$^2$ and Q$^3$ may particularly each independently represent CH, CX$^5$, N or N(O), preferably, Q$_1$ and Q$^3$ are CH and Q$^2$ is CH, CF, N or N(O).

Ar may also particularly represents a group (ii) where:
R$^9$ particularly represents:
(i) alkyl, for example C$_{1-4}$alkyl; or
(ii) alkoxy, for example C$_{1-4}$alkoxy); or
(iii) cycloalkyl, for example C$_{3-6}$cycloalkyl; or
(iv) aryl, for example optionally substituted phenyl; or
(v) aryloxy, for example optionally substituted phenoxy; or
(vii) heteroaryl, for example optionally substituted azaheteroaryl;

[It is to be understood that the aforementioned heteroaryl moieties represented by R$^9$ when containing at least one nitrogen atom may be presented as the corresponding N-oxides];

the moiety

is preferably

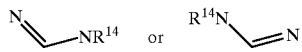

especially where R$^{14}$ represents a hydrogen atom or a methyl group, more especially where R$^{14}$ is hydrogen;

Q$^1$ may particularly represent CH, N or N(O), preferably, Q$^1$ is CH; and the moiety A$^2$ may particularly represent a direct bond or a straight- or branched-chain alkylene linkage containing from 1 to 4 carbon atoms, optionally substituted by alkoxy.

R$^7$ preferably represents a C$_{1-4}$alkyl group optionally substituted by one or more halogen (e.g. chlorine or fluorine) atoms, more preferably a methyl or difluoromethyl group;

Z$^1$ preferably represents an oxygen atom; and

Z$^2$ preferably represents an oxygen atom or a bond.

A further particular group of compounds of the present invention are compounds of formula (Ia)

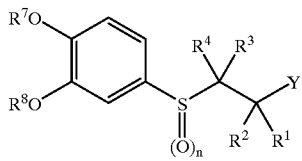

(Ia)

wherein R$^1$, R$^2$, R$^3$, R$^4$, R$^7$, R$^8$, and n are as defined previously and Y is carboxy or more preferably a —C(=O)NHOH group, N-oxides thereof and their prodrugs, pharmaceutically acceptable salts, and solvates (e.g. hydrates), thereof.

Compounds of formula (Ia) in which R$^7$ represents methyl or difluoromethyl are preferred, especially where R$^7$ is methyl.

Compounds of formula (Ia) in which R$^8$ represents a C$_{3-6}$cycloalkyl group (e.g. cyclopentyl) are preferred.

Compounds of formula (Ia) in which n is 2 are preferred.

A preferred group of compounds of the invention are compounds of formula (Ia) in which R$^1$, R$^2$, R$^3$ and R$^4$ are as defined previously, R$^7$ is methyl or difluoromethyl (especially methyl), R$^8$ is C$_{3-6}$cycloalkyl (e.g. cyclopentyl), n is 2, and Y represents —C(=O)NHOH, and N-oxides thereof, and their prodrugs, pharmaceutically acceptable salts, and solvates (e.g. hydrates), thereof.

A further particular group of compounds of the present invention are compounds of formula (Ib):

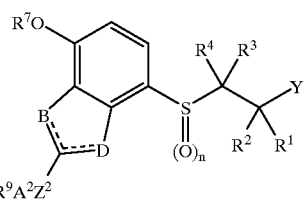

wherein $R^1$, $R^2$, $R^3$, $R^4$, $R^7$, $R^9$, $A^2$, $Z^2$,

are as defined previously and Y is carboxy preferably a —C(=O)—NHOH group and N-oxides thereof and their prodrugs, pharmaceutically acceptable salts, and solvates (e.g. hydrates), thereof.

Compounds of formula (Ib) in which $R^7$ represents methyl or difluoromethyl are preferred, especially where $R^7$ is methyl.

Compounds of formula (Ib) in which $R^9$ represents a straight- or branched-chain $C_{1-4}$alkyl group (e.g. isopropyl), a $C_{3-6}$cycloalkyl group (e.g. cyclopropyl), $C_{1-4}$alkoxy (e.g. methoxy), aryl, aryloxy, or heteroaryl (e.g. an azoheteroaryl group such as pyridyl) are preferred.

Compounds of formula (Ib) in which $A^2$ represents a direct bond are a preferred group of compounds. Compounds of formula (Ib) in which $A^2$ represents a straight or branched chain alkylene linkage containing from 1 to 6 carbon atoms, for example a methylene, ethylene, propylene, methylmethylene, or butylmethylene linkage, (especially methylene) are also a preferred group of compounds.

Compounds of formula (Ib) in which $A^2$ represents a straight or branched chain alkylene linkage containing from 1 to 6 carbon atoms which is substituted by alkoxy, for example a methoxymethylene or methoxypropylmethylene, are a further preferred group of compounds.

Compounds of formula (Ib) in which the moiety

represents

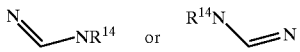

where
  $R^{14}$ represents a hydrogen atom or a methyl group (especially a hydrogen atom) are preferred.

Compounds of formula (Ib) in which $Z^2$ represents a direct bond are preferred.

A preferred group of compounds of the invention are compounds of formula (Ib) in which $R^1$, $R^2$, $R^3$ and $R^4$ are as previously defined, $R^7$ is methyl or difluoromethyl (especially methyl), $R^9$ is $C_{1-4}$alkyl (e.g. isopropyl), $C_{3-6}$cycloalkyl (e.g. cyclopropyl), $C_{1-4}$alkoxy (e.g. methoxy), aryl, aryloxy or heteroaryl (e.g. an azaheteroaryl group such as pyridyl), $A^2$ is a direct bond or a $C_{1-6}$alkylene chain (e.g. methylene) optionally substituted by alkoxy (e.g.methoxymethylene or methoxypropylmethylene),

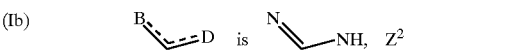

$Z^2$ is a direct bond, n is 2 and Y represents —C(=O)—NHOH, and N-oxides thereof, and their prodrugs, pharmaceutically acceptable salts, and solvates (e.g. hydrates), thereof.

Particular compounds for use according to the invention are selected from the following species:

3-(3-cyclopentyloxy-4-methoxyphenylsulfonyl)-7-phenylheptanohydroxamic acid;

3-(3-cyclopentyloxy-4-methoxyphenylsulfonyl)-5-phenylpentanohydroxamic acid;

3-(3-Cyclopentyloxy-4-methoxyphenylsulfonyl)-3-(thiophen-3-yl)-propionohydroxamic acid;

5-(4-butoxyphenyl)-3-(3-cyclopentyloxy-4-methoxyphenylsulfonyl)-pentanohydroxamic acid;

3-(3-benzyloxyphenyl)-3-(3-cyclopentyloxy-4-methoxyphenylsulfonyl)-propionohydroxamic acid;

3-(2-benzyloxyphenyl)-3-(3-cyclopentyloxy-4-methoxyphenylsulfonyl)-propionohydroxamic acid;

3-(3-benzyloxy-4-methoxyphenyl)-3-(3-cyclopentyloxy-4-methoxyphenylsulfonyl)-propionohydroxamic acid;

3-(3-cyclopentyloxy-4-methoxyphenylsulfonyl)-3-(3-phenoxyphenyl)-propionohydroxamic acid;

3-(3-cyclopentyloxy-4-methoxyphenylsulfonyl)-3-[3-(4-methoxyphenoxy)phenyl]-propionohydroxamic acid;

7-(benzo[1,3]dioxol-5-yl)-3-(3-cyclopentyloxy-4-methoxyphenylsulfonyl)-heptanohydroxamic acid;

3-(4-benzyloxyphenyl)-3-(3-cyclopentyloxy-4-methoxyphenylsulfonyl)-propionohydroxamic acid;

3-(3-cyclopentyloxy-4-methoxyphenylsulfonyl)-5-methyl-hexanohydroxamic acid;

3-(3-cyclopentyloxy-4-methoxyphenylsulfonyl)-octanohydroxamic acid;

3-(3-cyclopentyloxy-4-methoxyphenylsulfonyl)-7-phenylheptanohydroxamic acid;

3-(3-cyclopentyloxy-4-methoxyphenylsulfonyl)-5-(4-phenoxyphenyl)-pentanohydroxamic acid;

5-(4-benzyloxyphenyl)-3-(3-cyclopentyloxy-4-methoxyphenylsulfonyl)-pentanohydroxamic acid;

3-(3-cyclopentyloxy-4-methoxyphenylsulfonyl)-hexanohydroxamic acid;

3-[3-(4-chlorophenoxy)phenyl]-3-(3-cyclopentyloxy-4-methoxyphenylsulfonyl)-propionohydroxamic acid;

3-(3-cyclopentyloxy-4-methoxyphenylsulfonyl)-3-[3-(3,4-dichlorophenoxy)phenyl]-propionohydroxamic acid;

3-[3-(4-t-butyl-phenoxy)phenyl]-3-(3-cyclopentyloxy-4-methoxyphenylsulfonyl)-propionohydroxamic acid;

3-(3-bromo-4,5-dimethoxyphenyl)-3-(3-cyclopentyloxy-4-methoxyphenylsulfonyl)-butyrohydroxamic acid;

3-(3-cyclopentyloxy-4-methoxyphenylsulfonyl)-4-(N-methyl-N-benzoylamino)-pentanohydroxamic acid;

3-(3-cyclopentyloxy-4-methoxyphenylsulfonyl)-5-(N-methyl-N-benzoylamino)-butyrohydroxamic acid;

3-(3-cyclopentyloxy-4-methoxyphenylsulfonyl)-5-(N-methyl-N-phenylcarbamoyloxy)-pentanohydroxamic acid;

5-(benzyloxycarbonyl-N-methylamino)-3-(3-cyclopentyloxy-4-methoxyphenylsulfonyl)-pentanohydroxamic acid;

3-(3-cyclopentyloxy-4-methoxyphenylsulfonyl)-5-(N-methyl-N-phenylcarbamoyl)-pentanohydroxamic acid;

3-(3-cyclopentyloxy-4-methoxyphenylsulfonyl)-6-(N-methyl-N-phenylcarbamoyl)-hexanohydroxyamiacid;

3-(3-cyclopentyloxy-4-methoxyphenylsulfonyl)-6-(1,3-dioxo-1,3-dihydro-isoindol-2-yl)-hexanohydroxamic acid;

3-(3-cyclopentyloxy-4-methoxyphenylsulfonyl)-6-(3,4-dihydro-2H-quinolin-1-yl)-7-oxo-hexanohydroxamic acid;
3-(3-cyclopentyloxy-4-methoxyphenylsulfonyl)-5-(3,4-dihydro-2H-quinolin-1-yl)-5-oxo-pentanohydroxamic acid;
3-(3-cyclopentyloxy-4-methoxyphenyl)sulfanyl-7-phenylheptanohydroxamic acid;
3-(7-methoxy-2-methoxymethyl-3H-benzimidazol-4-yl)sulfonyl-7-phenylheptanohydroxamic acid;
3-(7-methoxy-2-cyclopropyl-3H-benzimidazol-4-yl)sulfonyl-7-phenylheptanohydroxamic acid;
3-(7-methoxy-2-methoxymethyl-3H-benzimidazol-4-ylsulfonyl)-7-phenylheptanohydroxamic acid;
3-(7-methoxy-2-cyclopropyl-3 H-benzimidazol-4-ylsulfonyl)-7-phenylheptanohydroxamic acid;
3-(4-methoxy-3-[trans-3-phenoxy-cyclopentyloxy]phenylsulphonyl)-7-phenylheptanohydroxamic acid;
3-(4-methoxy-3-[trans-3-(pyridin-2-yloxy)-cyclopentyloxy]phenylsulphonyl)-7-phenylheptanohydroxamic acid;
3-(4-methoxy-3-[trans-3-(pyridin-3-yloxy)-cyclopentyloxy]phenylsulphonyl)-7-phenylheptanohydroxamic acid;
3-(4-methoxy-3-[trans-3-(pyridin-4-yloxy)-cyclopentyloxy]phenylsulphonyl)-7-phenylheptanohydroxamic acid;
3-(4-methoxy-3-[cis-3-(pyridin-2-yloxy)-cyclopentyloxy]phenylsulphonyl)-7-phenylheptanohydroxamic acid;
3-(4-methoxy-3-[cis-3-(pyridin-3-yloxy)-cyclopentyloxy]phenylsulphonyl)-7-phenylheptanohydroxamic acid;
3-(3-[N-t-butoxycarbonylpyrrolidin-3-yloxy]-4-methoxyphenylsulphonyl)-7-phenylheptanohydroxamic acid;
3-(4-methoxy-3-[(N-phenyl)pyrrolidin-3-yloxy]phenylsulphonyl)-7-phenylheptanohydroxamic acid;
3-(4-methoxy-3-(2-phenyl-ethoxy)phenylsulphonyl)-7-phenylheptanohydroxamic acid;
3-(4-methoxy-3-(4-phenyl-butoxy)phenylsulphonyl)-7-phenylheptanohydroxamic acid;
3-(4-difluromethoxy-3-[2-phenylethoxy]phenylsulphonyl)-7-phenylheptanohydroxamic acid;
3-(4-methoxy-3-(2-benzyloxyethoxy)phenylsulphonyl)-7-phenylheptanohydroxamic acid;
3-(4-methoxy-3-(2-phenxyoxyethoxy)phenylsulphonyl)-7-phenylheptanohydroxamic acid;
3-(5-methoxy-4-[2-(4-methoxyphenyl)ethoxy]pyridin-2-ylsulphenyl)-7-phenylheptanohydroxamic acid;
3-(4-methoxy-3-(2-indanyloxy)phenylsulphonyl)-7-phenylheptanohydroxamic acid;
3-(4-methoxy-3-[2-(pyridin-2-yl)ethoxy]phenylsulphonyl)-7-phenylheptanohydroxamic acid;
3-(4-methoxy-3-[3-(pyridin-4-yl)propyloxy]phenylsulphonyl)-7-phenylheptanohydroxamic acid;
3-(4-methoxy-3-[3-(pyridin-3-yl)propyloxy]phenylsulphonyl)-7-phenylheptanohydroxamic acid;
3-(5-methoxy-4-[2-(pyridin-2-yl)ethoxy]pyridin-2-ylsulphonyl)-7-phenylheptanohydroxamic acid;
3-(4-methoxy-3-(2-thien-2-ylethoxy)phenylsulphonyl)-7-phenylheptanohydroxamic acid;
3-{3-{3-(4-chlorophenyl)-1,2,4-oxadiazol-5-ylmethoxy}-4-methoxyphenylsulphonyl)-7-phenylheptanohydroxamic acid;
3-{3-{3-(4-methoxyphenyl)-1,2,4-oxadiazol-5-ylmethoxy}-4-methoxyphenylsulphonyl)-7-phenylheptanohydroxamic acid;
3-(3-[3-(pyridin-2-yl)-1,2,4-oxadiazol-5-ylmethoxy]-4-methoxyphenylsulphonyl)-7-phenylheptanohydroxamic acid;
3-(3-[2-(4-chlorophenyl)-1,3,4-oxadiazol-5-ylmethoxy]-4-methoxyphenylsulphonyl)-7-phenylheptanohydroxamic acid;
3-(3-cyclopentyloxy-4-methoxyphenylsulfonyl)-5-phenylpentanoic acid;
3-(3-cyclopentyloxy-4-methoxyphenylsulfonyl)-3-(thiophen-3-yl)-propionic acid;
5-(4-butoxyphenyl)-3-(3-cyclopentyloxy-4-methoxyphenylsulfonyl)-pentanoic acid;
3-(3-benzyloxyphenyl)-3-(3-cyclopentyloxy-4-methoxyphenylsulfonyl)-propionic acid;
3-(2-benzyloxyphenyl)-3-(3-cyclopentyloxy-4-methoxyphenylsulfonyl)-propionic acid;
3-(3-benzyloxy-4-methoxyphenyl)-3-(3-cyclopentyloxy-4-methoxyphenylsulfonyl)-propionic acid;
3-(3-cyclopentyloxy-4-methoxyphenylsulfonyl)-3-(3-phenoxyphenyl)-propionic acid;
3-(3-cyclopentyloxy-4-methoxyphenylsulfonyl)-3-[3-(4-methoxyphenoxy)phenyl]-propionic acid;
7-benzo[1,3]dioxol-5-yl-3-(3-cyclopentyloxy-4-methoxyphenylsulfonyl)-heptanoic acid;
3-(4-benzyloxyphenyl)-3-(3-cyclopentyloxy-4-methoxyphenylsulfonyl)-propionic acid;
3-(3-cyclopentyloxy-4-methoxy-phenylsulfonyl)-5-methyl-hexanoic acid;
3-(3-cyclopentyloxy-4-methoxy-phenylsulfonyl)-octanoic acid;
3-(3-cyclopentyloxy-4-methoxy-phenylsulfonyl)-7-phenylheptanoic acid;
3-(3-cyclopentyloxy-4-methoxy-phenylsulfonyl)-5-(4-phenoxyphenyl)-pentanoic acid;
5-(4-benzyloxyphenyl)-3-(3-cyclopentyloxy-4-methoxy-phenylsulfonyl)-pentanoic acid;
3-(3-cyclopentyloxy-4-methoxyphenylsulfonyl)-hexanoic acid;
3-[3-(4-chlorophenoxy)-phenyl]-3-(3-cyclopentyloxy-4-methoxyphenylsulfonyl)-propionic acid;
3-(3-cyclopentyloxy-4-methoxy-phenylsulfonyl)-3-[3-(3,4-dichlorophenoxy)phenyl]-propionic acid;
3-[3-(4-t-butylphenoxy)-phenyl]-3-(3-cyclopentyloxy-4-methoxyphenylsulfonyl)-propionic acid;
3-(3-bromo-4,5-dimethoxyphenyl)-3-(3-cyclopentyloxy-4-methoxyphenylsulfonyl)-propionic acid;
3-(3-cyclopentyloxy-4-methoxyphenylsulfonyl)-3-(N-methyl-N-benzoyamino)-butanoic acid;
3-(3-cyclopentyloxy-4-methoxyphenylsulfonyl)-4-(N-methyl-N-benzoylamino)-pentanoic acid;
5-[N-methyl-N-phenylcarbamoyloxy]-3-(3-cyclopentyloxy-4-methoxyphenylsulfonyl)-pentanoic acid;
5-(benzyloxycarbonyl-N-methylamino)-[3-(3-cyclopentyloxy-4-methoxyphenylsulfonyl)-pentanoic acid;
3-(3-cyclopentyloxy-4-methoxyphenylsulfonyl)-5-(N-methyl-N-phenylcarbamoyl)-pentanoic acid;
3-(3-cyclopentyloxy-4-methoxyphenylsulfonyl)-6-(N-ethyl-Nphenylcarbamoyl)-heptanoic acid;
3-(3-cyclopentyloxy-4-methoxyphenylsulfonyl)-6-(1,3-dioxo-1,3-dihydro-isoindol-2-yl)-hexanoic acid
3-(3-cyclopentyloxy-4-methoxyphenylsulfonyl)-6-(3,4-dihydro-2H-quinolin-1-yl)-6-oxo-hexanoic acid
3-(3-cyclopentyloxy-4-methoxyphenylsulfonyl)-5-(3,4-dihydro-2H-quinolin-1-yl)5-oxo-pentanoic acid
3-(3-cyclopentyloxy-4-methoxyphenylsulfanyl)-7-phenylheptanoic acid;
3-(7-methoxy-2-methoxymethyl-3H-benzimidazol-4-yl)sulfonyl-7-phenylheptanoic acid;
3-(7-methoxy-2-cyclopropyl-3H-benzimidazol-4-yl)sulfonyl-7-phenylheptanoic acid;
3-(7-methoxy-2-methoxymethyl-3H-benzimidazol-4-ylsulfonyl)-7-phenylheptanohydroxamic acid;

3-(7-methoxy-2-cyclopropyl-3H-benzimidazol-4-ylsulfonyl)-7-phenylheptanohydroxamic acid;
3-(4-methoxy-3-[trans-3-phenoxy-cyclopentyloxy]phenylsulphonyl)-7-phenylheptanohydroxamic acid;
3-(4-methoxy-3-[trans-3-(pyridin-2-yloxy)-cyclopentyloxy]phenylsulphonyl)-7-phenylheptanohydroxamic acid;
3-(4-methoxy-3-[trans-3-(pyridin-3-yloxy)-cyclopentyloxy]phenylsulphonyl)-7-phenylheptanohydroxamic acid;
3-(4-methoxy-3-[trans-3-(pyridin-4-yloxy)-cyclopentyloxy]phenylsulphonyl)-7-phenylheptanohydroxamic acid;
3-(4-methoxy-3-[cis-3-(pyridin-2-yloxy)-cyclopentyloxy]phenysulphonyl)-7-phenylheptanohydroxamic acid;
3-(4-methoxy-3-[cis-3-(pyridin-3-yloxy)-cyclopentyloxy]phenylsulphonyl)-7-phenylheptanohydroxamic acid;
3-(3-[N-t-butoxycarbonylpyrrolidin-3-yloxy]-4-methoxyphenylsulphonyl)-7-phenylheptanohydroxamic acid;
3-(4-methoxy-3-[(N-phenyl)pyrrolidin-3-yloxy]phenylsulphonyl)-7-phenylheptanohydroxamic acid;
3-(4-methoxy-3-(2-phenyl-ethoxy)phenylsulphonyl)-7-phenylheptanohydroxamic acid;
3-(4-methoxy-3-(4-phenyl-butoxy)phenylsulphonyl)-7-phenylheptanohydroxamic acid;
3-(4-difluoromethoxy-3-[2-phenylethoxy]phenylsulphonyl)-7-phenylheptanohydroxamic acid;
3-(4-methoxy-3-(2-benzyloxyethoxy)phenylsulphonyl)-7-phenylheptanohydroxamic acid;
3-(4-methoxy-3-(2-phenoxyethoxy)phenylsulphonyl)-7-phenylheptanohydroxamic acid;
3-(5-methoxy-4-[2-(4-methoxyphenyl)ethoxy]pyridin-2-ylsulphonyl)-7-phenylheptanohydroxamic acid;
3-(4-methoxy-3-(2-indanyloxy)phenylsulphonyl)-7-phenylheptanohydroxamic acid;
3-(4-methoxy-3-[2-(pyridin-2-yl)ethoxy]phenylsulphonyl)-7-phenylheptanohydroxamic acid;
3-(4-methoxy-3-[3-(pyridin-4-yl)propyloxy]phenylsulphonyl)-7-phenylheptanohydroxamic acid;
3-(4-methoxy-3-[3-(pyridin-3-yl)propyloxy]phenylsulphonyl)-7-phenylheptanohydroxamic acid;
3-(5-methoxy-4-[2-(pyridin-2-yl)ethoxy]pyridin-2-ylsulphonyl)-7-phenylheptanohydroxamic acid;
3-(4-methoxy-3-(2-thien-2-ylethoxy)phenylsulphonyl)-7-phenylheptanohydroxamic acid;
3-(3-{3-(4-chlorophenyl)-1,2,4-oxadiazol-5-ylmethoxy}-4-methoxyphenylsulphonyl)-1-phenylheptanohydroxamic acid;
3-(3-{3-(4-methoxyphenyl)-1,2,4-oxadiazol-5-ylmethoxy}-4-methoxyphenylsulphonyl)-1-phenylheptanohydroxamic acid;
3-(3-[3-(pyridin-2-yl)-1,2,4-oxadiazol-5-ylmethoxy]-4-methoxyphenylsulphonyl)-7-phenylheptanohydroxamic acid;
3-(3-[2-(4-chlorophenyl)-1,3,4-oxadiazol-5-ylmethoxy]-4-methoxyphenylsulphonyl)-7-phenylheptanohydroxamic acid;
and the corresponding N-oxides, and their prodrugs, pharmaceutically acceptable salts, and solvates (e.g. hydrates). Preferred compounds include:
3-(3-cyclopentyloxy-4-methoxyphenylsulfonyl)-7-phenylheptanohydroxamic acid;
3-(7-methoxy-2-methoxymethyl-3H-benzimidazol-4-ylsulfonyl)-7-phenylheptanohydroxamic acid;
3-(7-methoxy-2-cyclopropyl-3H-benzimidazol-4-ylsulfonyl)-7-phenylheptanohydroxamic acid;
3-(4-methoxy-3-[trans-3-phenoxy-cyclopentyloxy]phenylsulphonyl)-7-phenylheptanohydroxamic acid;
3-(4-methoxy-3-[trans-3-(pyridin-2-yloxy)-cyclopentyloxy]phenylsuphonyl)-7-phenylheptanohydroxamic acid;
3-(4-methoxy-3-[trans-3-(pyridin-3-yloxy)-cyclopentyloxy]phenylsulphonyl)-7-phenylheptanohydroxamic acid;
3-(4-methoxy-3-[trans-3-(pyridin-4-yloxy)-cyclopentyloxy]phenylsulphonyl)-7-phenylheptanohydroxamic acid;
3-(4-methoxy-3-[cis-3-(pyridin-2-yloxy)-cyclopentyloxy]phenylsulphonyl)-7-phenylheptanohydroxamic acid;
3-(4-methoxy-3-[cis-3-(pyridin-3-yloxy)-cyclopentyloxy]phenylsulphonyl)-7-phenylheptanohydroxamic acid;
3-(3-[N-t-butoxycarbonylpyrrolidin-3-yloxy]-4-methoxyphenylsulphonyl)-7-phenylheptanohydroxamic acid;
3-(4-methoxy-3-[(N-phenyl)pyrrolidin-3-yloxy]phenylsulphonyl)-7-phenylheptanohydroxamic acid;
3-(4-methoxy-3-(2-phenyl-ethoxy)phenylsulphonyl)-7-phenylheptanohydroxamic acid;
3-(4-methoxy-3-(4-phenyl-butoxy)phenylsulphonyl)-7-phenylheptanohydroxamic acid;
3-(4-difluoromethoxy-3-[2-phenylethoxy]phenylsulphonyl)-7-phenylheptanohydroxamic acid;
3-(4-methoxy-3-(2-benzyloxyethoxy)phenylsulphonyl)-7-phenylheptanohydroxamic acid;
3-(4-methoxy-3-(2-phenoxyethoxy)phenylsulphonyl)-7-phenylheptanohydroxamic acid;
3-(5-methoxy-4-[2-(4-methoxyphenyl)ethoxy]pyridin-2-ylsulphonyl)-7-phenylheptanohydroxamic acid;
3-(4-methoxy-3-(2-indanyloxy)phenylsulphonyl)-7-phenylheptanohydroxamic acid;
3-(4-methoxy-3-[2-(pyridin-2-yl)ethoxy]phenylsulphonyl)-7-phenylheptanohydroxamic acid;
3-(4-methoxy-3-[3-(pyridin-4-yl)propyloxy]phenylsulphonyl)-7-phenylheptanohydroxamic acid;
3-(4-methoxy-3-[3-(pyridin-3-yl)propyloxy]phenylsulphonyl)-7-phenylheptanohydroxamic acid;
3-(5-methoxy-4-[2-(pyridin-2-yl)ethoxy]pyridin-2-ylsulphonyl)-7-phenylheptanohydroxamic acid;
3-(4-methoxy-3-(2-thien-2-ylethoxy)phenylsulphonyl)-7-phenylheptanohydroxamic acid;
3-(3-{3-(4-chlorophenyl)-1,2,4-oxadiazol-5-ylmethoxy}-4-methoxyphenylsulphonyl)-7-phenylheptanohydroxamic acid;
3-(3-{3-(4-methoxyphenyl)-1,2,4-oxadiazol-5-ylmethoxy}-4-methoxyphenylsulphonyl)-7phenylheptanohydroxamic acid;
3-(3-[3-(pyridin-2-yl)-1,2,4-oxadiazol-5-ylmethoxy]-4-methoxyphenylsulphonyl)-7-phenylheptanohydroxamic acid;
3-(3-[2-(4-chlorophenyl)-1,3,4-oxadiazol-5-ylmethoxy]-4-methoxyphenylsulphonyl)-7-phenylheptanohydroxamic acid;
and the corresponding N-oxides, and their prodrugs, pharmaceutically acceptable salts, and solvates (e.g. hydrates).

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention exhibit marked pharmacological activities according to tests described in the literature which tests results are believed to correlate to pharmacological activity in humans and other mammals. Detailed in vitro and in vivo procedures are described hereinafter.

Compounds of the invention are inhibitors of tumor necrosis factor, especially TNF-alpha. Thus, in a further embodiment, the present invention provides compounds of the invention and compositions containing compounds of the invention for use in the treatment of a patient suffering from, or subject to, conditions which can be ameliorated by the administration of an inhibitor of TNF, especially of TNF-alpha. For example, compounds of the present invention are useful in joint inflammation, including arthritis, rheumatoid arthritis and other arthritic conditions such as rheumatoid spondylitis and osteoarthritis. Additionally, the compounds are useful in the treatment of sepsis, septic shock, gram negative sepsis, toxic shock syndrome, adult respiratory distress syndrome, asthma and other chronic pulmonary diseases, bone resorption diseases, reperfusion injury, graft vs. host reaction, allograft rejection and leprosy. Furthermore, the compounds are useful in the treatment of infections such as viral infections and parasitic infections, for example malaria such as cerebral malaria, fever and myalgias due to infection, HIV, AIDS, cachexia such as cachexia secondary to AIDS or to cancer.

Compounds of the invention are also cyclic AMP phosphodiesterase inhibitors, in particular type IV cyclic AMP phosphodiesterase inhibitors. Thus, in another embodiment of the invention, we provide compounds of the invention and compositions containing compounds of the invention for use in the treatment of a patient suffering from, or subject to, conditions which can be ameliorated by the administration of an inhibitor of cyclic AMP phosphodiesterase, especially type IV cyclic AMP phosphodiesterase. For example, compounds within the present invention are useful as bronchodilators and asthma-prophylactic agents and agents for the inhibition of eosinophil accumulation and of the function of eosinophils, e.g. for the treatment of inflammatory airways disease, especially reversible airway obstruction or asthma, and for the treatment of other diseases and conditions characterized by, or having an etiology involving, morbid eosinophil accumulation. As further examples of conditions which can be ameliorated by the administration of inhibitors of cyclic AMP phosphodiesterase such as compounds of the invention there may be mentioned inflammatory diseases, such as atopic dermatitis, urticaria, allergic rhinitis, psoriasis, rheumatoid arthritis, inflammatory diseases (e.g. ulcerative colitis and Crohn's disease), adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication.

Another group of conditions which may be treated with the compounds of the present invention includes diseases and disorders of the central nervous system such as brain trauma, ischaemia, Huntington's disease and tardive dyskinaesia.

Other disease states which may be treated with the compounds of the present invention include pyresis, autoimmune diseases (e.g. systemic lupus erythematosus, allergic erythematosus, multiple sclerosis), type I diabetes mellitus, psoriasis, Bechet's disease, anaphylactoid purpura nephritis, chronic glomerulonephritis and leukemia.

A special embodiment of the therapeutic methods of the present invention is the treating of asthma.

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of cyclic AMP phosphodiesterase or of TNF, especially TNF-alpha, for example conditions as hereinbefore described, which comprises the administration to the patient of an effective amount of compound of the invention or a composition containing a compound of the invention. "Effective amount" is meant to describe an amount of compound of the present invention effective in inhibiting cyclic AMP phosphodiesterase and/or TNF and thus producing the desired therapeutic effect.

According to another aspect of the invention, there is provided the use of a compound of the invention in the manufacture of a medicament for the treatment of a patient suffering from, or subject to, conditions which can be ameliorated by the administration of an inhibitor of cyclic AMP phosphodiesterase, especially type IV cyclic AMP phosphodiesterase.

According to a further aspect of the invention, there is provided the use of a compound of the invention in the manufacture of a medicament for the treatment of a patient suffering from, or subject to, conditions which can be ameliorated by the administration of an inhibitor of TNF, especially of TNF-alpha.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient. Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention. The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day. The compounds of the present invention may also be formulated for use in conjunction with other therapeutic agents such as agents which increase cyclic AMP production including β-agonists and $PGE_2$. It is to be understood that the present invention includes combinations of compounds of the present invention with one or more of the aforementioned therapeutic agents.

Compounds of the invention may be prepared by the application or adaptation of known methods, which means methods used heretofore or described in the literature, for example as illustrated in the Examples and Reference Examples and chemical equivalents thereof.

Those skilled in the art will appreciate how to choose the reaction conditions in the following processes so as to avoid or minimise unwanted side-reactions.

For example, when a starting material contains ester moieties, any alcohol or ester used as reaction medium is preferably chosen so as to avoid transesterification.

Those skilled in the art will also appreciate how to avoid or minimise unwanted side-reactions by the judicious and timely protection and deprotection of reactive functional groups, for example hydroxy, amino, imino, thio or carboxy groups, for example as illustrated in this specification.

Conventional protecting groups may be used in accordance with standard practice, for examples see T. W. Green and P. G. M. Wuts in "Protective Groups in Organic Chemistry" John Wiley and Sons, 1991.

Compounds of this invention where Ar, $R^1$, $R^2$, $R^3$, $R^4$, and Y are as hereinbefore defined, n is 2 and $A^1$ is a direct bond or a straight or branched $C_{1-4}$alkylene chain, may be prepared by oxidation of compounds of formula (I) where Ar, $R^1$, $R^2$, $R^3$, $R^4$, and Y are as hereinbefore defined, n is 0 or 1 and $A^1$ is a direct bond or a straight or branched $C_{1-4}$alkylene chain. The oxidation may conveniently be carried out by means of reaction with oxone® in an inert solvent such as aqueous methanol at a temperature from about 0° C. to about room temperature. Alternatively, the oxidation may be carried out by reaction with a mixture of hydrogen peroxide and an organic acid, e.g. acetic acid, preferably at about room temperature. Alternatively, the oxidation may be carried out by reaction with a peracid, for example peracetic acid or m-chloroperoxybenzoic acid, in an inert solvent such as hexane, chloroform or dichloromethane, at a temperature at about room temperature.

Compounds of this invention where Ar, $R^1$, $R^2$, $R^3$, $R^4$, and Y are as hereinbefore defined, n is 1 and $A^1$ is a direct bond or a straight or branched $C_{1-4}$alkylene chain, may be prepared by oxidation of compounds of formula (I) where Ar, $R^1$, $R^2$, $R^3$, $R^4$, and Y are as hereinbefore defined, n is 0 and $A^1$ is a direct bond or a straight or branched $C_{1-4}$alkylene chain. The oxidation may conveniently be carried out by means of reaction with m-chloroperoxybenzoic acid, in an inert solvent such as hexane, chloroform or dichloromethane, at a temperature at about room temperature.

In a process (A), compounds of formula (I) wherein Ar, $R^1$, $R^2$, $R^3$, and $R^4$ are as hereinbefore defined, n is 0, 1 or 2, $A^1$ is a direct bond or a straight or branched $C_{1-4}$alkylene chain, and Y is a group —C(=O)—NHOH, may be prepared by using resin technology as shown in scheme 1.

SCHEME 1

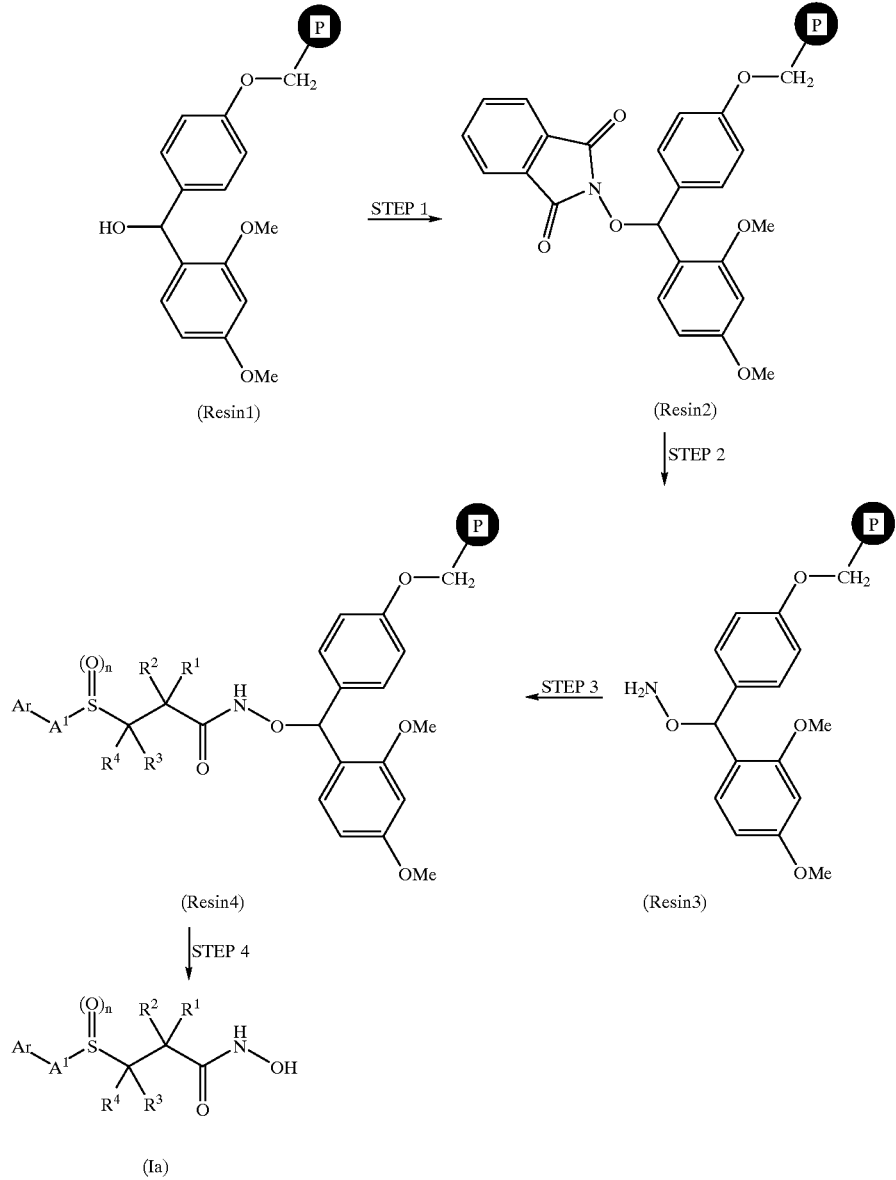

For example Rink acid resin [Resin1,4-(2,4'-dimethoxyphenyl-hydroxymethyl)-phenoxy resin] is treated, in Step 1, with N-hydroxyphthalimide in the presence of a sulphonic acid such as benzene sulfonic acid or camphor sulphonic acid at a temperature at about 50° C. to give the 4-(2', 4'-dimethoxyphenyl-N-phthalimidyloxymethyl)-phenoxy resin (Resin2).

Resin2 is then treated, in Step 2, with hydrazine hydrate in an inert solvent such as tertiary butanol at a temperature at about 60° C. to give the 4-[aminooxy-(2',4'-dimethoxyphenyl)-methyl]-phenoxy-resin (Resin3).

Resin3 may then be coupled, as in Step 3, with an acid of general formula (I) wherein Ar, $R^1$, $R^2$, $R^3$, $R^4$ and n are as hereinbefore defined, $A^1$ is a direct bond or a straight or branched $C_{1-4}$alkylene chain and Y is carboxy, to give the hydroxamate ester resin (Resin4). The coupling reaction may conveniently be carried out in the presence of a carbodiimide, such as 1-(3-dimethylaminopropyl)-3-ethylcarbodiimide, in an inert solvent such as dimethylformamide and at a temperature at about room temperature. Resin4 may then be treated with an acid, such as trifluoroacetic acid, in an inert solvent such as dichloromethane to liberate the hydroxamic acid of general formula (I) wherein Ar, $R^2$, $R^3$, $R^4$ and n are as hereinbefore defined, $A^1$ is a direct bond or a straight or branched $C_{1-4}$alkylene chain and Y is a group —C(=O)—NHOH.

As another example compounds of formula (I) wherein Ar, $R^1$, $R^2$, $R^3$, $R^4$ and n are as hereinbefore defined, $A^1$ is a direct bond or a straight or branched $C_{1-4}$alkylene chain, and Y is a group —C(=O)—NHOH, may be prepared by reaction of compounds of formula (I), wherein Ar, $R^1$, $R^2$, $R^3$, $R^4$ and n are as hereinbefore defined, $A^1$ is a direct bond or a straight or branched $C_{1-4}$alkylene chain and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid. The preparation may also be carried out using O-benzylhydroxylamine followed by hydrogenation in the presence of a suitable metal catalyst, e.g. platinum or palladium optionally supported on an inert carrier such as carbon, preferably in a solvent such as methanol or ethanol.

As another example compounds of formula (I) wherein Ar, $R^1$, $R^2$, $R^3$, $R^4$ and n are as hereinbefore defined, $A^1$ is a direct bond or a straight or branched $C_{1-4}$alkylene chain and Y is a group —C(=O)—NHOH, may be prepared by reaction of compounds of formula (II):

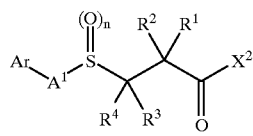

(II)

wherein Ar, $R^1$, $R^2$, $R^3$, $R^4$ and n are as hereinbefore defined, $A^1$ is a direct bond or a straight or branched $C_{1-4}$alkylene chain and $X^2$ is chloro or bromo, with hydroxylamine in an inert solvent, such as tetrahydrofuran and at a temperature at about room temperature.

In a process (B), compounds of formula (I) wherein Ar, $R^3$ and n are as hereinbefore defined, $R^1$, $R^2$, and $R^4$ are hydrogen, $A^1$ is a direct bond or a straight or branched $C_{1-4}$alkylene chain and Y is a carboxy, may be prepared using resin technology as shown in scheme 2.

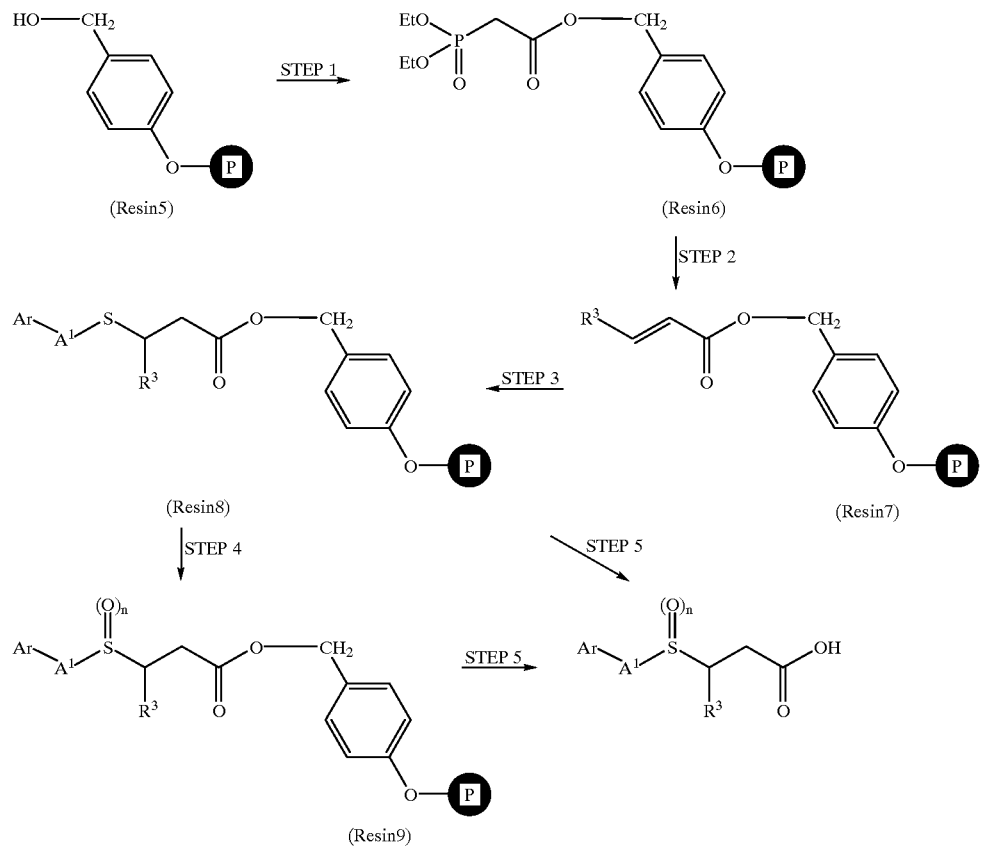

SCHEME 2

For example Wang resin (Resin5) is treated, in Step 1, with diethyl phosphonoacetic acid in an inert solvent such as dimethylformamide in the presence of 2,6-dichlorobenzoyl choride and pyridine at a temperature at about room temperature to give the esterified resin (Resin6).

The diethylphosphonoacetoxy-resin (Resin6) is treated, in Step 2, with a base such as potassium bis(trimethylsilyl)amide in an inert solvent such as toluene, at a temperature at about 0° C., followed by reaction with an aldehyde of general formula (12):

$R^3$—CHO  (III)

wherein $R^3$ is as hereinbefore defined, at a temperature at about room temperature to give the alkenoate resin (Resin7).

Resin7 may then be reacted, as in Step 3, with a thiol of general formula (13):

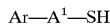(IV)

wherein Ar is as hereinbefore defined and $A^1$ is a direct bond or a straight or branched $C_{1-4}$alkylene chain, to give the alkanoate resin (Resin8). The Michael addition may be conveniently carried out under mild basic conditions, for example in the presence of lithium hydroxide and at a temperature at about room temperature.

Resin8 may then be hydrolysed by treatment with an acid, such as trifluoroacetic acid, in an inert solvent such as dichloromethane, to liberate acids of general formula (I) wherein Ar and $R^3$ are as hereinbefore defined, $R^1$, $R^2$, and $R^4$ are hydrogen, $A^1$ is a direct bond or a straight or branched $C_{1-4}$alkylene chain, n is 0 and Y is carboxy.

Resin8 may also be treated with an oxidising agent such as m-chloroperbenzoic acid in an inert solvent, such as dioxane, and at a temperature at about room temperature to give Resin9.

Resin9 may then be hydrolysed by treatment with an acid, such as trifluoroacetic acid, in an inert solvent such as dichloromethane, to liberate acids of general formula (I) wherein Ar and $R^3$ are as hereinbefore defined, $R^1$, $R^2$, and $R^4$ are hydrogen, $A^1$ is a direct bond or a straight or branched $C_{1-4}$alkylene chain, m is 1 or 2 and Y is carboxy.

As another example compounds of formula (I) wherein Ar, $R^1$, $R^2$, $R^3$, $R^4$ and n are as hereinbefore defined, $A^1$ is a direct bond or a straight or branched $C_{1-4}$alkylene chain and Y is carboxy, may be prepared by hydrolysis of esters of formula (V):

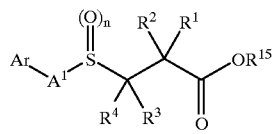(V)

wherein Ar, $R^1$, $R^2$, $R^3$, $R^4$ and n are as hereinbefore defined, $A^1$ is a direct bond or a straight or branched $C_{1-4}$alkylene chain and $R^{15}$ is alkyl, alkenyl or arylalkyl.

As another example compounds of formula (I) wherein Ar, $R^1$, $R^2$, $R^3$, $R^4$ and n are as hereinbefore defined, $A^1$ is a direct bond or a straight or branched $C_{14}$alkylene chain and Y is carboxy, may be prepared by reaction of esters of formula (V) wherein Ar, $R^1$, $R^2$, $R^3$, $R^4$ and n are as hereinbefore defined, $A^1$ is a direct bond or a straight or branched $C_{1-4}$alkylene chain and $R^{15}$ is allyl, by reaction with tetrakis(triphenylphosphine)palladium(0) in the presence of triphenylphosphine and acetic acid, in an inert solvent such as tetrahydrofuran and at ambient temperature.

As another example compounds of formula (I) wherein Ar, $R^1$, $R^3$, $R^4$ and n are as hereinbefore defined, $A^1$ is a direct bond or a straight or branched $C_{1-4}$alkylene chain, $R^2$ is hydrogen and Y is carboxy or a group —C(=O)—NHOH, may be prepared by reaction of compounds of formula (VI):

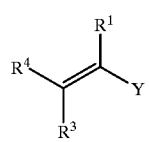(VI)

wherein $R^1$, $R^3$, and $R^4$ as hereinbefore defined, and Y is carboxy or —C(=O)NHOH, with compounds of formula (IV, Ar—$A^1$—SH) wherein Ar is as hereinbefore defined and $A^1$ is a direct bond or a straight or branched $C_{1-4}$alkylene chain. The addition reaction may be conveniently carried out in an inert solvent such as tetrahydrofuran or toluene in the presence of a base for example triethylamine, piperidine or sodium hydride, at a temperature from about room temperature to about reflux temperature. The reaction may also be carried out in the absence of solvent in a sealed vessel at a temperature at about 100° C., this is particularly suitable when the base is piperidine.

As another example compounds of formula (I) wherein Ar, $R^1$, $R^2$ and $R^3$ are as hereinbefore defined, $R^4$ is hydrogen, $A^1$ is a direct bond or a straight or branched $C_{1-4}$alkylene chain, n is zero and Y is carboxy, may be prepared by reaction of compounds of formula (VII):

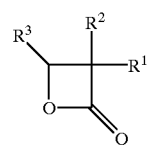(VII)

wherein $R^1$, $R^2$ and $R^3$ are as hereinbefore defined with compounds of formula (IV, Ar—$A^1$—SH) wherein Ar is as hereinbefore and $A^1$ is a direct bond or a straight or branched $C_{1-4}$alkylene chain, in the presence of a base such as sodium hydroxide or in an alcohol for example isopropanol and at a temperature from about 0° C. to about room temperature. The reaction may also be carried out in the presence of cesium carbonate in dimethylformamide.

As another example compounds of formula (I) wherein Ar is as hereinbefore defined, $R^2$ and $R^4$ form a bond, $R^1$ and $R^3$ together with the carbon atoms to which they are attached form a heteroaryl ring (for example pyrazolyl), n is 2, $A^1$ is a direct bond or a straight or branched $C_{1-4}$alkylene chain and Y is carboxy, may be prepared by reaction of compounds of formula (VIII):

(VIII)

wherein $R^6$ is as hereinbefore defined, with compounds of formula (IX):

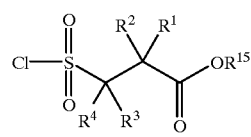(IX)

wherein $R^2$ and $R^4$ form a bond, $R^1$ and $R^3$ together with the carbon atoms to which they are attached form a heteroaryl ring (for example pyrazolyl), and $R^{15}$ is as hereinbefore defined, in the presence of sodium hydroxide in aqueous tetrahydrofuran at reflux. An example of (IX) is methyl 5-chlorosulphonyl-pyrazol-4-yl carboxylate (s.Vega, S.Vega, J.Het.Chem.,1993,30, p1509).

The starting materials and intermediates may be prepared by the application or adaptation of known methods, for example methods as described in the Reference Examples or their obvious chemical equivalents.

Intermediates of formula (II) wherein Ar, $R^1$, $R^2$, $R^3$ and $R^4$ are as hereinbefore defined, $A^1$ is a direct bond or alkylene, n is 0, 1 or 2 and $X^2$ is a halogen atom, may be prepared from the corresponding acids of formula (I)

wherein Ar, $R^1$, $R^2$, $R^3$, $R^4$ and n are as hereinbefore defined, $A^1$ is a direct bond or a straight or branched $C_{1-4}$alkylene chain and Y is —$CO_2H$, by the application or adaptation of known methods for the preparation of acid halides from carboxylic acids, for example when $X^2$ represents a chlorine atom the reaction may be carried out by means of thionyl chloride or, preferably, oxalyl chloride, optionally in the presence of a small amount of dimethylformamide.

Intermediates of formula (IV) wherein Ar is as hereinbefore defined and $A^1$ is a direct bond, may be prepared by reduction of compounds of formula (1):

Ar—S—S—Ar (1)

wherein Ar is as hereinbefore defined with sodium borohydride in an inert solvent such as tetrahydrofuran at a temperature at about room temperature.

Alternatively intermediates of formula (IV) wherein Ar is as hereinbefore defined and $A^1$ is a direct bond) may be prepared from compounds of formula (2):

Ar—Br (2)

wherein Ar is as hereinbefore, by reaction with sodium thiobenzoate and subsequent hydrolysis (as described by A. Osuka et. al. Synthesis, 1983, p.68).

Compounds of formula (1) wherein Ar is as hereinbefore defined may be prepared by butanol (20ml) for ten minutes then treated with hydrazine hydrate (10 ml). The mixture was heated to 60° C., reagents of formula (3):

Ar—MgBr (3)

wherein Ar is as hereinbefore defined, with sulphur, in an inert solvent, for example an ether, e.g. tetrahydrofuran, preferably at a temperature from about 0° C. to about room temperature.

Grignard reagents of formula (3) wherein Ar is as hereinbefore defined may be prepared by reaction of the appropriate bromobenzene of formula (2) wherein Ar is as hereinbefore defined, with magnesium in an inert solvent such as tetrahydrofuran in the presence of an alkylhalide for example 1,2-dibromethane, at reflux temperature.

Compounds of formula (2), wherein Ar is a group (i) [where $R^7$ and $R^8$ are as hereinbefore defined, $Z^1$ and $Z^2$ are oxygen, $Q^1$, $Q^2$ and $Q^3$ are CH, and $A^2$ represents a direct bond or a straight- or branched-chain $C_{1-6}$alkylene linkage]), may be prepared by reaction of a bromophenol of formula (4);

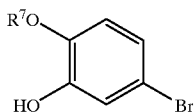

(4)

with compounds of formula (5):

$R^8A^2OH$ (5)

wherein $R^8$ is as hereinbefore defined and $A^2$ represents a direct bond or a straight- or branched-chain $C_{1-6}$alkylene linkage. The reaction may be carried out in the presence of a triarylphosphine, such as triphenylphosphine, and a dialkyl ester, such as the diisopropyl or diethyl ester of azodicarboxylic acid. The reaction preferably takes place in an inert solvent, such as tetrahydrofuran, preferably at a temperature from about 0° C. to about 60° C.

Intermediates of formula (V) wherein Ar, $R^1$, $R^2$, $R^3$, $R^4$ and $R^{15}$ are as hereinbefore defined, $A^1$ is a direct bond or a straight or branched $C_{1-4}$alkylene chain and n is 1 or 2, may be prepared by oxidation of compounds of formula (V) wherein Ar, $R^1$, $R^2$, $R^3$, $R^4$ and $R^{15}$ are as hereinbefore defined, $A^1$ is a direct bond or a straight or branched $C_{1-4}$alkylene chain and n is 0. The oxidation may conveniently be carried out by means of reaction with oxone® in an inert solvent such as aqueous methanol at a temperature from about 0° C. to about room temperature. Alternatively, the oxidation may be carried out by reaction with a mixture of hydrogen peroxide and an organic acid, e.g. acetic acid, preferably at about room temperature. Alternatively, the oxidation may be carried out by reaction with a peracid, for example peracetic acid or m-chloroperoxybenzoic acid, in an inert solvent such as hexane, chloroform or dichloromethane, at a temperature at about room temperature.

Intermediates of formula (V) wherein Ar, $R_1$, $R^3$, $R^4$ and $R^{15}$ are as hereinbefore defined, $R^2$ is hydrogen, $A^1$ is a direct bond or a straight or branched $C_{1-4}$alkylene chain and n is zero, may be prepared by reaction of compounds of formula (6):

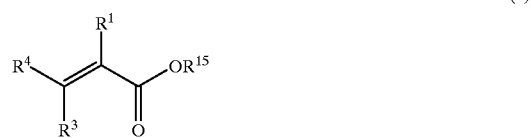

(6)

wherein $R^1$, $R^3$, $R^4$ and $R^{15}$ are as hereinbefore defined, with compounds of formula (IV) wherein Ar is hereinbefore defined and $A^1$ is a direct bond or a straight or branched $C_{1-4}$alkylene chain. The reaction preferably takes place in the presence of a base such as an alkyllithium, for example butyllithium, in an inert solvent such as tetrahydrofuran and at a temperature from about 0C to about room temperature.

Intermediates of formula (V) wherein Ar, $R^1$, $R^2$, $R^3$, $R^4$ and $R^{15}$ are as hereinbefore defined, $A^1$ is a direct bond or a straight or branched $C_{1-4}$alkylene chain and n is zero, may be prepared by reaction of compounds of formula (7):

(7)

wherein $R^1$, $R^2$, $R^3$, $R^4$ and $R^{15}$ are as hereinbefore defined, and L is a leaving group such as a halogen atom or an aryl- or alkyl-sulphonyloxy group (e.g. methane- or p-toluenesulphonyloxy); with a thiol of general formula (IV), wherein Ar is as hereinbefore defined and $A^1$ is a direct bond or a straight or branched $C_{1-4}$alkylene chain. The reaction may be conveniently carried out in the presence of a base such as: a trialkylamine, for example triethylamine; an alkali metal carbonate, such as potassium carbonate; or an alkali metal hydroxide, such as potassium hydroxide, in an inert solvent such as tetrahydrofuran or dimethylformamide, and at a temperature from about room temperature to about 60° C.

Intermediates of formula (V) wherein Ar, $R^3$ and $R^{15}$ are as hereinbefore defined, $A^1$ is a direct bond or a straight or branched $C_{1-4}$alkylene chain, $R^2$ and $R^4$ together form a bond, $R^1$ is hydrogen and n is zero, may be prepared by reaction of compounds of formula (7) wherein $R^1$, $R^3$ and $R^{15}$ are as hereinbefore defined, $R^2$ and $R^4$ together form a bond and L is halo, preferably chloro, with thiols of formula (IV) wherein Ar is as hereinbefore defined and $A^1$ is a direct bond or a straight or branched $C_{1-4}$alkylene chain, in the presence of a base such as potassium carbonate and in a solvent such as methanol or dimethylformamide and at a temperature from about room temperature to about 60° C.

Compounds of formula (6) wherein $R^1$, $R^3$, $R^4$ and $R^{15}$ are as hereinbefore defined, may be prepared by reaction of compounds of formula (8):

(8)

wherein $R^3$ and $R^4$ are as hereinbefore defined, with a dialkylphosphonate of formula (9):

$(RO)_2P(=O)CH(R^1)C(=O)OR^{15}$     (9)

wherein $R^1$ and $R^{15}$ is as hereinbefore defined and R is alkyl, for example ethyl. The reaction preferably takes place in the presence of a base, for example sodium hydride, in an inert solvent such as tetrahydrofuran and at a temperature at about room temperature.

Compounds of formula (7) wherein $R^1$, $R^2$, $R^3$, $R^4$ and $R^{15}$ are as hereinbefore defined, and L is a leaving group such as an aryl- or alkyl-sulphonyloxy group (e.g. methane- or p-toluene-sulphonyloxy) may be prepared by reaction of alcohols of formula (10):

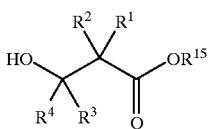

(10)

with the appropriate aryl- or alkyl-sulfonyl chloride (e.g. e.g. methane- or p-toluene-sulphonyl chloride) in the presence of a suitable base, such as pyridine or triethylamine, in an organic solvent, such as dichloromethane and at a temperature at about room temperature.

Compounds of formula (7) wherein $R^1$, $R^3$ and $RI^5$ are as hereinbefore defined, $R^2$ and $R^4$ together form a bond and L is chloro, may be prepared by reaction of β-ketoesters of formula (11):

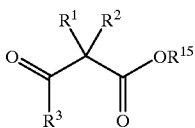

(11)

wherein $R^1$, $R^3$ and $R^{15}$ are as hereinbefore defined, and $R^2$ is hydrogen, with phosphorus pentachloride in an inert solvent such as hexane and at a temperature at about reflux. Compounds of formula (7) wherein $R^{15}$ is as hereinbefore defined, $R^1$ and $R^3$ together with the carbon atoms to which they are attached form a cycloalkyl ring, for example cyclopentyl, which is optionally substituted by alkyl, arylalkyl or heteroarylalkyl, $R^2$ and $R^4$ together form a bond and L is chloro, may be similarly prepared from , ketoesters of formula (10) wherein $R^{15}$ is as hereinbefore defined, $R^1$ and $R^3$ together with the carbon atoms to which they are attached form a cycloalkyl ring, for example cyclopentyl, which is optionally substituted by alkyl, arylalkyl or heteroarylalkyl, and $R^2$ is hydrogen. Compounds of formula (10) wherein $R^1$, $R^3$ and $R^{15}$ are as hereinbefore defined, and $R^2$ and $R^4$ are hydrogen, may be prepared by reduction of β-ketoesters of formula (11) wherein $R^1$, $R^2$, $R^3$ and $R^{15}$ are as hereinbefore defined. The selective reduction may be carried out using sodium borohydride in methanol at a temperature at about room temperature.

β-Hydroxy-esters of formula (10) wherein $R^1$, $R^2$ and $R^{15}$ are as hereinbefore defined, and $R^3$ and $R^4$ are hydrogen, may be prepared by reduction of acids of formula (12):

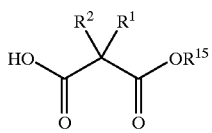

(12)

wherein $R^1$, $R^2$ and $R^{15}$ are as hereinbefore defined. The selective reduction may be carried out using diborane in an organic solvent such as tetrahydrofuran at about 0C to about 40° C.

β-Hydroxy-esters of formula (10) wherein $R^1$, $R^2$, $R^3$, $R^4$ and $R^{15}$ are as hereinbefore defined, may be prepared by reaction of compounds of formula (8) wherein $R^3$ and $R^4$ are as hereinbefore defined with esters of formula $R^1CH(R^2)CO_2R^{15}$ wherein $R^1$, $R^2$ and $R^{15}$ are as hereinbefore defined, in the presence of lithium diisopropylamine in an inert solvent such as tetrahydrofuran and at a temperature from about −78° C. to about 0° C.

β-Ketoesters of formula (11) wherein $R^1$ and $R^{15}$ is as hereinbefore defined, $R^3$ is a group $—L^1—R^5$ [where $L^1$ is a straight or branched $C_{2-6}$alkylene chain and $R^5$ is as defined hereinbefore] and $R^2$ is hydrogen, may be prepared by: initial alkylation of an acetoacetate ester, such as methyl acetoacetate, using an alkyl halide $R^1—X$ (where $R^1$ is as hereinbefore defined and X is halogen, preferably bromo) in the presence of an alkali metal carbonate such as potassium carbonate in an inert solvent, such as acetone or dimethylformamide, and at a temperature from about room temperature to about 50° C.; and subsequent alkylation with an alkyl halide $R^5—L^2—CH_2—X$ [where $R^5$ is as hereinbefore defined, $L^2$ is a direct bond or a straight or branched $C_{1-6}$alkylene chain and X is halo, preferably bromo], in the presence of sodium hydride in an inert solvent such as dimethylformamide.

β-Ketoesters of formula (11) wherein $R^{15}$ is as hereinbefore defined, $R^2$ is hydrogen and $R^3$ and $R^5$ each represent a group $—L^1—R^5$ [where $L^1$ is a straight or branched $C_{2-6}$alkylene chain and $R^5$ is as hereinbefore defined], may be prepared by alkylation of the dianion of an acetoacetate ester using an alkyl halide $R^5—L^2—CH_2—X$ [where $L^2$ and $R^5$ are as hereinbefore defined and X is halo, preferably bromo).

3-Alkyl-(arylalkyl- or heteroarylalkyl-)-2-oxo-cyclopentanecarboxylic acid esters of formula (11) wherein $R^{15}$ is as hereinbefore defined $R^1$ and $R^3$ together with the carbon atoms to which they are attached form a cycloalkyl ring (for example cyclopentyl), which is optionally substituted by alkyl, arylalkyl or heteroarylalkyl, and $R^2$ is hydrogen, may be prepared by alkylation of the dianion of a 2-oxo-cycloalkylcarboxylic acid ester (for example methyl 2-oxo-cyclopentanecarboxylate), with an alkyl-arylalkyl- or heteroarylalkyl halide. The dianion is generated by initial reaction with sodium hydride in an inert solvent such as tetrahydrofuran in the presence of a base such as sodium hydride at room temperature, followed by reaction with butyllithium at a temperature at about −25° C.

Compounds of formula (12) wherein $R^1$, $R^2$ and $R^{15}$ are as hereinbefore defined, may be prepared by hydrolysis of compounds of formula (13):

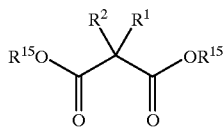

(13)

wherein $R^1$, $R^2$ and $R^{15}$ are as hereinbefore defined by using one equivalent of hydroxide (such as sodium or potassium hydroxide) in an aqueous alcohol or tetrahydrofuran solvent at about 20° C. to about 90° C.

Compounds of formula (13) wherein $R^1$, $R^2$ and $R^{15}$ are as hereinbefore defined, may be prepared for example by alkylation of a dialkyl malonate, such as diethyl malonate, to introduce the group $R^1$ and then where appropriate, subsequent alkylation to introduce the group $R^2$ (i.e. when $R^2$ is alkyl). The alkylation may be carried out using an alkyl halide $R^1$—X, and then where appropriate $R^2$—X (where X is halogen, preferably bromo), in the presence of a suitable base such as an alkali metal carbonate (such as potassium or sodium carbonate), hydroxide (such as sodium or potassium hydroxide) or alkoxide (such as sodium methoxide or ethoxide), in a polar solvent such as ethanol at a temperature from about 20° C. to about 90° C.

Intermediates of formula (VI) wherein $R^1$, $R^3$ and $R^4$ are as hereinbefore defined, and Y is carboxy, may be prepared by hydrolysis of compounds of formula (6) wherein $R^1$, $R^3$, $R^4$ and $R^{15}$ are as hereinbefore defined. When $R^{15}$ is t-butyl the hydrolysis is conveniently carried out under acidic conditions, for example in the presence of trifluoroacetic acid.

Intermediates of formula (VI) wherein $R^1$, $R^3$ and $R^4$ are as hereinbefore defined, and Y is —C(=O)NHOH, may be prepared by reaction of compounds of formula (VI) wherein $R^1$, $R^3$ and $R^4$ are as hereinbefore defined, and Y is carboxy, according to the procedures described hereinbefore for the conversion of compounds of formula (I) where Y is carboxy to compounds of formula (I) where Y is —C(=O)—NHOH.

Intermediates of formula (VII) wherein $R^1$, $R^2$ and $R^3$ are as hereinbefore defined, may be prepared by cyclisation of βhydroxy-acids of formula (14):

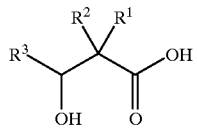

(14)

wherein $R^1$, $R^2$ and $R^3$ are as hereinbefore defined, in the presence of a sulphonyl chloride, for example benzenesulphonyl chloride, in the presence of pyridine and at a temperature at about room temperature.

β- Hydroxy-acids of formula (14) wherein $R^1$, $R^2$ and $R^3$ are as hereinbefore defined, may be prepared by hydrolysis of ,hydroxy-esters of formula (10) wherein $R^1$, $R^2$, $R^3$ and $R^{15}$ are as hereinbefore defined and $R^4$ is hydrogen.

β-Hydroxy-acids of formula (14) wherein $R^3$ is as hereinbefore defined and $R^1$ and $R^2$ together with the carbon atom to which they are attached form a $C_{3-6}$cycloalkyl ring (e.g. cyclopentyl), may be prepared by reacting a $C_{3-6}$cycloalkyl carboxylic acid (e.g. cyclopentane carboxylic acid) with lithium diisopropylamide, in an inert solvent such as tetrahydrofuran and subsequent reaction of the so formed dianion with an aldehyde of formula $R^3$—CHO, wherein $R^3$ is as hereinbefore defined, at a temperatute at about —78° C.

β-Hydroxy-acids of formula (14) wherein $R^1$ and $R^3$ are each independently a group —$L^1$—$R^5$ (where $L^1$ is $C_{1-6}$alkylene, preferably tetramethylene, or a $C_{2-6}$alkylene containing an oxygen or sulphur atom, and $R^5$ is as hereinbefore defined, preferably phenyl), $R^2$ is hydrogen, and with defined stereochemistry at C-2 and C-

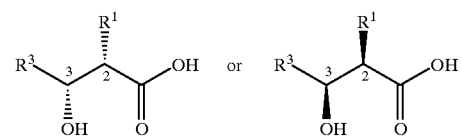

, may be prepared by reaction of compounds of formula

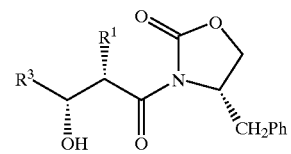

(15a)

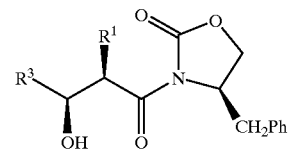

(15b)

may be prepared by reaction of compounds of formula wherein $R^1$ and $R^3$ are as defined immediately above, with hydrogen peroxide in the presence of lithium hydroxide in aqueous tetrahydrofuran at a temperature below 10° C.

β-Hydroxy-acids of formula (14) wherein $R^1$ and $R^3$ are each independently a group —$L^1$—$R^5$ (where $L^1$ is $C_{1-6}$alkylene, preferably tetramethylene, or a $C_{2-6}$alkylene containing an oxygen or sulphur atom, and $R^5$ is as hereinbefore defined, preferably phenyl), $R^2$ is hydrogen, and with defined stereochemistry at C-2 and C-

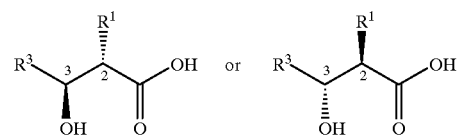

may be prepared by hydrolysis of esters of formula (16a)

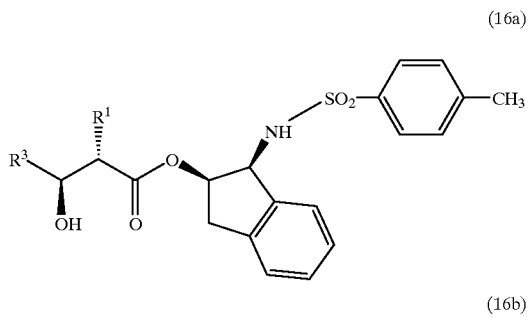

(16b)

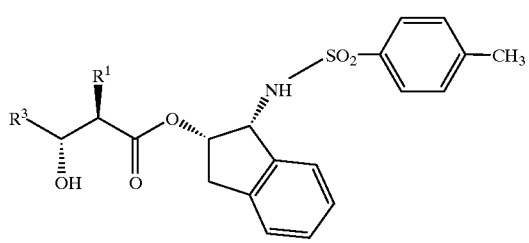

wherein $R^1$ and $R^3$ are as defined immediately above. The hydrolysis may conveniently be carried out using lithium hydroxide in aqueous tetrahydrofuran at room temperature.

Compounds of formula (15a) wherein $R^1$ and $R^3$ are as defined immediately above, may be prepared by reaction of compounds of formula (17):

(17)

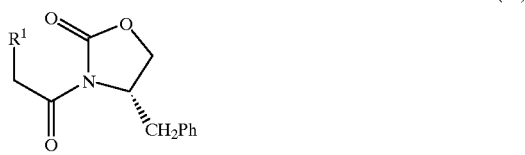

wherein $R^1$ and $R^{15}$ are as defined immediately above, with compounds of formula $R^3$—CHO wherein $R^3$ is as defined immediately above in the presence of dibutyl boron triflate and triethylamine in an inert solvent such as dichloromethane and a temperature from −78° C. to about 0C. Compounds of (15b) may be similarly prepared from the (R)— enantiomer of (17).

Compounds of formula (16a) wherein $R^1$ and $R^3$ are as defined immediately above may be prepared by reaction of (1S,2R)-cis-1-toluenesulphonamide-2-hydroxyindane with acids of formula $R^3$—$CO_2H$ wherein $R^3$ is as defined immediately above, in the presence of dicyclohexylcarbodiimide and dimethylaminopyridine in an inert solvent such as dichloromethane at room temperature (according to the procedure of A. Ghosh, Tetrahedron Letters, 1995, p.6811). Compounds of formula (16b) wherein $R^1$ and $R^3$ are as defined immediately above may be similarly prepared by from (1R,2S)-cis-1-toluenesulphonamide-2-hydroxyindane Compounds of formula (17) wherein $R^1$ is as defined immediately above may be prepared by reaction of (S)-4-benzyl-2-oxazolidinone with butyl lithium, in an inert solvent such as tetrahydrofuran and at a temperature at about −78° C., and subsequent reaction with a mixed anhydride of formula (18):

$$R^3\text{—C}(=O)\text{—O—C}(=O)C(CH_3)_3 \quad (18)$$

wherein $R^3$ is as defined immediately above. The (R)- enantiomer of (17) may be similarly prepared from 4-(R)-benzyl-2-oxazolidinone.

Compounds of formula (18), wherein $R^3$ is as defined immediately above, may be prepared by reacting acids of formula $R^3$—$CO_2H$ wherein $R^3$ is as defined immediately above, with trimethylacetylchloride in the presence of triethylamine in an inert solvent such as tetrahydrofuran at a temperature at about 0° C.

Compounds of formula (VIII) wherein Ar is as hereinbefore defined and $R^6$ is hydrogen, may be prepared by hydrogenation of compounds of formula (19):

$$Ar\text{—}NO_2 \quad (19)$$

wherein Ar is as hereinbefore defined. The hydrogenation may be carried out using hydrogen in the presence of a suitable metal catalyst, e.g. palladium optionally supported on an inert carrier such as carbon, preferably in a solvent such as ethanol.

Compounds of formula (19), wherein Ar is a group (i) [where $R^7$ and $R^8$ are as hereinbefore defined, $Z^1$ and $Z^2$ are oxygen, $Q^1$, $Q^2$ and $Q^3$ are CH, and $A^2$ represents a straight- or branched-chain $C_{1-6}$alkylene linkage], may be prepared by reaction of compounds of formula (20):

(20)

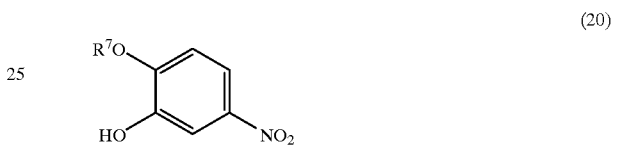

wherein $R^7$ is as hereinbefore defined, with alcohols of formula (5) wherein $R^8$ is as hereinbefore defined and $A^2$ represents a straight- or branched-chain $C_{1-6}$alkylene linkage, in the presence of a triarylphosphine, such as triphenylphosphine, and a dialkyl ester, such as the diisopropyl or diethyl ester of azodicarboxylic acid. The reaction preferably takes place in an inert solvent, such as tetrahydrofuran, preferably at a temperature from about 0° C. to about 60° C. Intermediates of formulae (resin1), (resin8), (resin9), (II), (IV), (V), (VI), (VII), (VIII), (1), (2), (3), (7), (10), (15a), (15b), (16a), (16b), (19) are novel compounds and, as such, they and their processes described herein for their preparation constitute further features of the present invention.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad. In the mass spectra abbreviations have the following meanings: APCI, Atmospheric Pressure Chemical Ionization, using a Micromass Platform II instrument with a Source Temperature of 250° C. and a Probe Temperature of 450° C. with nitrogen as the Nebulizing Gas; Isp, Ion spray, using a SCIEX API III instrument at room temperature with nitrogen as the Nebulizing Gas and an ionisation voltage of 5 KV; FAB, Fast Atom Bombardment using a VG 70 SE instrument with Ar° atom to bombard the surface and 8 KV, I mA; Loop, Direct Injection; LC/MS, High Pressure Liquid Chromatography (using a Keystone BDS Hypersil $C_{18}$, 3μ, 4.6×50 mm column under gradient elution conditions with 0.1% trifluoroacetic acid in aqueous acetonitrile (from 10% to 100% acetonitrile over 10 minutes) as mobile phase and a flow rate of 1.0 ml/minute) followed by Mass Spectroscopy. Intra-Red spectra, IR(micro) on potassium bromide sample support, were determined using a Nicolet 740 FTIR w/IRPLAN Microscope instrument with Transmission spectra recorded at 4 cm$^{-1}$ resolution.

EXAMPLE 1

(±)-3-(3-Cyclopentyloxy-4-methoxyphenylsulfonyl)-7-phenylheptanohydroxamic acid

A stirred solution of (±)-3-(3-cyclopentyloxy-4-methoxyphenylsulfanyl)-7-phenylheptanohydroxamic acid (0.26 g, Example 3) in methanol (10 ml), at 0° C., was treated with a solution of OXONE®, potassium peroxymonosulphate, (0.54 g) in water (10 ml). The resulting white suspension was allowed to warm to room temperature and then stirred overnight. The mixture was concentrated to half volume then partitioned between water (50 ml) and ethyl acetate (50 ml). The aqueous layer was extracted twice with ethyl acetate (25 ml). The combined organic phases were washed with brine (50 ml), then dried over magnesium sulphate and then evaporated. The residue was subjected to flash chromatography on silica eluting with a mixture of petroleum ether and ethyl acetate (1:2, v/v) to give the title compound which was obtained as a white foam (0.14 g) after trituration with chloroform, m.p. 60–62° C. NMR [(CD$_3$)$_2$SO]: δ1.18–2.00 (m, 14H), 2.13 (m,1H), 2.45 (br t,2H), 2.75 (br s,1H), 3.50 (br s,1H), 3.80 (s,3H), 4.86 (br s,1H), 7.02–7.28 (m, 7H), 7.38 (d,1H), 8.88 (s,1H), 10.52 (s,1H). Mass spectrum (FAB): m/z 475 (M)$^+$.

EXAMPLE 2

(a) (±)-3-(3-Cyclopentyloxy-4-methoxyphenylsulfonyl)-5-1-phenyipentanohydroxamic acid Step 1: Rink acid resin [1 g, 4-(2',4'-dimethoxyphenyl-hydroxymethyl)-phenoxy resin, from Advanced ChemTech] was swelled in dimethylformamide (10 ml) for 15 minutes at ambient temperature then treated with N-hydroxyphthalimide (0.514 g) followed by benzene sulfonic acid (19 mg). The mixture was stirred at 50° C. for five hours, then cooled to ambient temperature and stirring continued for an additional 12 hours. The mixture was filtered and the resin was washed: (i) five times with dimethylformamide (25 ml), (ii) five times with a mixture of dimethylformamide and water (25 ml, 7:3, v/v), (iii) ten times with tetrahydrofuran (25 ml), (iv) ten times with diethyl ether (25 ml). The resin was dried overnight under high vacuum at 40° C. The IR spectrum of the 4-(3',4'-dimethoxyphenyl-N-phthalimidyloxymethyl)-phenocy resin shows a carbonyl absorbance at 1733 cm$^{-1}$. [Elemental analysis: N,0.26%. Calculated for a loading level of 0.18 mmol/g; N,0.28%].

Step 2: The 4-2',4'-dimethoxyphenyl-N-phthalimidyloxymethyl)-phenoxy resin (1 g) was swelled in tert-butanol (20 ml) for ten minutes then treated with hydrazine hydrate (10 ml). The mixture was heated to 60° C., with stirring, for 12 hours then cooled to ambient temperature. The mixture was filtered and the resin was washed: (i) ten times with dimethylformamide (25 ml), (ii) ten times with tetrahydrofuran (25 ml), (iv) ten times with diethyl ether (25 ml). After drying overnight under high vacuum at 40° C. 4-[aminooxy-(2',4'-dimethoxyphenyl)-methyl]-phenoxy-copoly(styrene-1%-divinylbenzene)-resin (100–200 mesh) was obtained. [Elemental Analysis: N,0.43%. Calculated for a loading level of 0.3 mmol/g: N,0.42%]. By proceeding in a similar manner but using camphor sulfonic acid instead of benzene sulfonic acid in Step 1 there was obtained an additional batch of 4-[aminooxy-(2',4'-dimethoxyphenyl)-methyl]-phenoxy-copoly(styrene-1%-divinylbenzene)-resin (100–200 mesh). [Elemental Analysis: N,0.57%. Calculated for a loading level of 0.38 mmol/g: N,0.54%].

Step 3: The 4-[aminooxy-(2',4'-dimethoxyphenyl)-methyl]-phenoxy-copoly(styrene-1%-divinylbenzene)-resin (0.1 g, batch with a loading level of 0.3 mmol/g) was swelled in anhydrous dimethylformamide (1 ml) for 15 minutes then treated with 1-(3-dimethylaminopropyl)-3-ethylcarbodiimide hydrochloride (0.03 g) followed by a solution of 3-(3-cyclopentyloxy-4-methoxy-benzenesulfonyl)-5-phenylpentanoic acid (0.067 g, Example 3)in anhydrous dimethylformamide (1 ml). The mixture was shaken for 20 hours. The resin was filtered and then washed successively three times with dimethylformamide, three times with water, three times with dimethylformamide, ten times with tetrahydrofuran and ten times with diethyl ether. The resin was then dried in vacuo at 40° C. for 20 hours.

Step 4: The dried resin from step 3 (0.1 g) was treated with trifluoroacetic acid in dichloromethane (2 ml, 1:9) for 1 hour, then filtered, and then washed twice with dichloromethane (1 ml). The combined filtrate and washings were evaporated to give the title compound (13.8 mg). Mass spectrum (APCI; Loop): m/z 448 (M+H)$^+$.

By proceeding in a manner similar to Example 2(a) but using the appropriate acid to replace 3-(3-cyclopentyloxy-4-methoxyphenylsulfonyl)-5-phenylpentanoic there was prepared:

(b) (±)-3-(3-Cyclopentyloxy-4-methoxphenylsulfonyl)-3-(thiophen-3-yl)-propionohydroxamic acid. Mass spectrum (APCI; Loop): m/z 426 (M+H)$^+$.

(c) (±)-5-(4-Butoxyphenyl)-3-(3-cyclopentyloxy-4-methoxyphenylsulfonyl)-pentanohydroxamic acid. Mass spectrum (APCI; Loop): m/z 520 (M+H)$^+$.

(d) (±)-3-(3-Benzyloxyphenyl)-3-(3-cyclopentyloxy-4-methoxyphenyisulfonyl)-propionohydroxamic acid. Mass spectrum (APCI; Loop): m/z 526 (M+H)$^+$.

(e) (±)-3-(2-Benzyloxyphenyl)-3-(3-cyclopenlyoxy-4-methoxyphenylsulfonyl)-propionohydroxamic acid. Mass spectrum (APCI; Loop): m/z 526 (M+H)$^+$.

(f) (±)-3-(3-Benzyloxy-4-methoxyphenyl)-3-(3-cyclopentyloxy-4-methoxyphenylsulfonyl) propionohydroxamic acid. Mass spectrum (APCI; Loop): m/z 556 (M+H)$^+$.

(g) (±)-3-(3-cyclopenlyoxy-4-methoxyphenylsulfonyl)-3-(3-phenoxyphenyl)-propionohydroxamic acid. Mass spectrum (APCI; Loop): m/z 512 (M+H)$^+$.

(h) (±)-3-(3-cyclopentyloxy-4-methoxyphenylsulfonyl)-3-[3-(4-methoxyphenoxy)-phenyl]-propionohydroxamic acid. Mass spectrum (APCI; Loop): m/z 542 (M+H)$^+$.

(i) (±)-7-(Benzo[1,3]dioxol-5-yl)-3-(3-cyclopentyloxy-4-methoxyphenylsulfonyl)-heptanohydroxamic acid. Mass spectrum (APCI; Loop): m/z 520 (M+H)$^+$.

(j) (±)-3-(4-Benzyloxyphenyl)-3-(3-cyclopentyloxy-4-methoxyphenylsulfonyl)-propionohydroxamic acid. Mass spectrum (APCI; Loop): m/z 526 (M+H)$^+$.

(k) (±)-3-(3-Cyclopentyloxy-4-methoxyphenylsulfonyl)-5-methyl-hexanohydroxamic acid. Mass spectrum (APCI; Loop): m/z 400 (M+H)$^+$.

(l) (±)-3-(3-Cyclopentyloxy-4-methoxyphenylsufonyl)-octanohydroxamic acid. Mass spectrum (APCI; Loop): m/z 414 (M+H)$^+$.

(n) (±)-3-(3-Cyclopentyloxy-4-methoxyphenylsulfonyl)-7-phenylheptanohydroxamic acid [Example 1(a)]. Mass spectrum (APCI; LCMS): m/z 478 (M+2+H)$^+$.

(o) (±)-3-(3-Cyclopentyloxy-4-methoxyphenylsulfonyl)-5-(4-phenonlphenyl)-pentanohydroxamic acid. Mass spectrum (APCI; Loop): m/z 540 (M+H)+.
(p) (±)-5-(4-Benzyloxyphenyl)-3-(3-cyclopentyloxy-4-methoxyphenylsulfonyl)-pentanohydroxamic acid. Mass spectrum (APCI; Loop): m/z 554 (M+H)+.
(q) (±)-3-(3-Cyclopentyloxy-4-methoxyphenylsulfonyl)-hexanohydroxamic acid. Mass spectrum (APCI; Loop) m/z 386 (M+H)+.
(r) (±)-3-[3-(4—Chlorophenoxy)phenyl]-3-(3-cyclopentyloxy-4-methoxyphenylsulfonyl)-propionohydroxamic acid. Mass spectrum (APCI; Loop): m/z 546 (M+H)+.
(s) (±)-3-(3-Cyclopenlyloxy-4-methoxyphenylsulfonyl)-3-[3-(3,4-dichlorophenoxy)phenyl]propionohydroxamic acid. Mass spectrum (APCI; Loop): m/z 580 (M+H)+.
(t) (±)-3-[3-(4-t-Butyl-phenoxy)phenyl]-3-(3-cyclopentyloxy-4-methoxyphenylsulfonyl)-propionohydroxamic acid. Mass spectrum (APCI; Loop): m/z 568 (M+H)+.
(u) (±)-3-(3-Bromo-4,5-dimethoxyphenyl)-3-(3-cyclopenlyloxy-4-methoxyphenylsulfonyl)-propionohydroxamic acid. Mass spectrum (APCI; Loop): m/z 557 (M+H)+.
(v) (±)-3-(3-Cyclopentyloxy-4-methoxyphenylsulfonyl)-4-(N-methyl—N-benzoylamino)-butyrohydroxamic acid. Mass spectrum (APCI; Loop): m/z 491 (M+H)+.
(w) (±)-3-(3-cyclopentyloxy-4-methoxyphenylsulfonyl)-5-(N-methyl—N-benzoylamino)-pentanohydroxamic acid. Mass spectrum (APCI; Loop): m/z 505 (M+H)+.
(x) (±)-3-(3-cyclopentyloxy-4-methoxyphenylsulfonyl)-5-(N-methyl—N-phenylcarbamoyloxy)-pentanohydroxamic acid. Mass spectrum (APCI; Loop): m/z 506 (M+H)+-15
(y) (±)-5-(Benzyloxycarbonyl—N-methylamino)-3-(3-Cyclopentyloxy-4-methoxyphenylsulfonyl)-pentanohydroxamic acid. Mass spectrum (APCI; Loop): m/z 535 (M+H)+.
(z) (±)-3-(3-Cyclopentyloxy-4-methoxyphenylsulfonyl)-5-(N-methyl—N-phenylcarbamoyl)-pentanohydroxamic acid. Mass spectrum (APCI; Loop): m/z 505 (M+H)+.
(aa) (±)-3-(3-Cyclopenlyloxy-4-methoxyphenylsulfonyl)-6-(N-methyl—N-phenylcarbamoyl)-hexanohydroxyamic acid. Mass spectrum (APCI; Loop): m/z 519 (M+H)+.
(ab) (±)-3-(3-Cyclopentyloxy-4-methoxyphenylsulfonyl)-6-(1,3-dioxo-1,3-dihydro-isoindol-2-yl)-hexanohydroxamic acid. Mass spectrum (APCI; Loop): m/z 531 (M+H)+.
(ac) (±)-3-(3-Cyclopentyloxy-4-methoxyphenylsulfonyl)-6-(3,4-dihydro-2H-guinolin-1-yl)-7-oxo-hexanohydroxamic acid. Mass spectrum (APCI; Loop): m/z 545 (M+H)+.
(ad) (±)-3-(3-Cyclopentyloxy-4-methoxyphenylsulfonyl)-5-(3,4-dihydro-2H-guinolin-1-yl)-5-oxo-pentanohydroxamic acid. Mass spectrum (APCI; Loop): m/z 531 (M+H)+.

EXAMPLE 3

(±)-3-(3-Cyclopentyloxy-4-methoxyphenyl)sulfanyl-7-phenylheptanohydroxamic acid

A stirred solution of (±)-3-(3-cyclopentyloxy-4-methoxyphenyl)sulfanyl-7-phenylheptanoic acid (0.40 g, Example 4) in a mixture of dimethylformamide (0.07 ml) and dichloromethane (20 ml) was treated dropwise with a solution of oxalyl chloride in dichloromethane (1.17 ml, 2.0 M). After stirring at room temperature for a further 30 minutes the mixture was treated dropwise with O-(trimethylsilyl)hydroxylamine (0.57 ml). The resulting white suspension was stirred for 10 minutes then partitioned between hydrochloric acid (50 ml, 1N) and ethyl acetate (50 ml). The aqueous layer was extracted twice with ethyl acetate (50 ml). The combined organic phases were washed with water (50 ml), then with brine (50 ml), then dried over magnesium sulphate and then evaporated to give the title compound (0.26 g) as a white foam. NMR (CDCl$_3$): δ1.60 (m,8H), 1.86 (m,6H), 2.35 (br d,2H), 2.60 (br t,2H), 3.30 (m,1H), 3.80 (s,3H), 3.73 (m,1H), 6.76 (d,1H), 6.95 (d,2H), 7.10–7.30 (m,5H). Mass spectrum (FAB): m/z 444 (M+H)+.

EXAMPLE 4

(a) (±)-3-(3-Cyclopentyloxy-4-methoxyphenylsulfonyl)-5-phenylpentanoic acid

STEP 1: Wang resin (20.0 g, from Advanced ChemTech) was swelled in anhydrous dimethylformamide (300 ml) for 15 minutes then treated with a solution of diethyl phosphonoacetic acid (8.83 g) in dimethylformamide (50 ml), then pyridine (7.12 g) and then 2,6-dichlorobenzoyl chloride (9.4 g). The mixture was agitated for 20 hours at room temperature. The resin was filtered and then washed successively three times with dimethylformamide, three times with water, three times with dimethylformamide, ten times with tetrahydrofuran and ten times with diethyl ether. The resin was then dried in vacuo at 40° C. for 20 hours. IR(micro): υc=o, 1738 cm$^{-1}$ STEP 2: The loaded resin from Step 1 (1.0 g) was swelled in anhydrous tetrahydrofuran (10 ml) for 15 minutes then treated with a solution of potassium bis(trimethylsilyl)amide in toluene (4 ml, 0.5M) at 0° C. The mixture was allowed to warm up to room temperature, then shaken for 30 minutes. The solvent was then drained to the top of the resin and the mixture treated with anhydrous cyclohexane (10 ml) then with hydrocinnamaldehyde (0.27 g). This mixture was shaken for approximately 72 hours at room temperature. The resin was filtered and then washed successively three times with dimethylformamide, three times with water, three times with dimethylformamide, ten times with tetrahydrofuran and ten times with diethyl ether. The resin was then dried in vacuo at 40° C. for 20 hours. IR(micro): υc=o, 1719 cm$^{-1}$ STEP 3: The resin from Step 2 (0.25 g) was swelled in anhydrous tetrahydrofuran (4 ml) for 15 minutes then treated with lithium hydroxide monohydrate (15 mg) followed by 3-cyclopentyloxy-4-methoxybenzene thiol (0.45 g, Reference Example 2). The mixture was shaken for approximately 36 hours at room temperature. The resin was filtered and then washed successively three times with dimethylformamide, three times with water, three times with dimethylformamide, ten times with tetrahydrofuran and ten times with diethyl ether. The resin was then dried in vacuo at 40° C. for 20 hours. IR(micro): υc=o, 1732 cm$^{-1}$ STEP 4: The resin from Step 3 (0.25 g) was swelled in 1,4-dioxane (5 ml) for 15 minutes then treated with a solution of m-chloroperoxybenzoic acid (0.44 g) in 1,4-dioxane (2 ml). The mixture was shaken for 16 hours. The resin was filtered and then washed successively three times with dimethylformamide, three times with water, three times with dimethylformamide, ten times with tetrahydrofuran and ten times with diethyl ether. The resin was then dried in vacuo at 40° C. for 20 hours.

STEP 5: The resin from Step 4 (0.25 g) was treated with a mixture of trifluoroacetic acid in dichloromethane (3 ml, 1:1, v/v) for 2 hours. The resin was filtered and then washed twice with dichloromethane (1 ml). The combined filtrate and washings were evaporated to give (±)-3-(3-cyclopentyloxy-4-methoxyphenylsulfonyl)-5-phenylpentanoic acid (68.3 mg). NMR(CDCl₃): δ1.50–2.05 (m,8H),230(m,1H),2.55–3.00(m,4H),3.55(m,1H),3.90(s, 3H),4.70(m,1H),6.95(d,1H), 7.05–7.30(m, 6H), Mass specturm (APCI; Loop): m/z 450 (M+NH₄)⁺, 433 (M+H)⁺.

By proceeding in a manner similar to Example 3(a) but using the appropriate aldehyde to replace hydrocinnamaldehyde in Step 2 there was prepared:

(b) (±)-3-(3—Cyoloentyloxy-4-methoxyphenylsulfonyl)-3-(thiophen-3-yl)-propionic acid as a thick brown oil, Mass Spectrum (APCI; Loop): m/z 411(M+H)⁺.

(c) (±)-5-(4-Butoxyphenyl)-3-(3-cyclopentyloxn-4-methoxyphenylsulfonyl)-pentanoic acid as a thick brown oil, Mass Spectrum (APCI; Loop): m/z 505(M+H)⁺.

(d) (±)-3-(3-Benzyloxyphenyl)-3-(3-cyclo(3entloxy-4-methoxyphenylsulfonyl)-propionic acid as a thick brown oil, Mass Spectrum (APCI; Loop): m/z 511(M+H)⁺.

(e) (±)-3-(2-Benzyloxyphenyl)-3-(3-cyclopentylox-4-methoxyphenylsulfonyl)-propionic acid as a thick brown oil, Mass Spectrum (APCI; Loop): m/z 511(M+H)⁺.

(f) (±)-3-(3-Benzyloxy-4-methoxyphenyl)-3-(3-cyclopentyloxy-4-methoxyphenylsulfonyl)-propionic acid as a thick brown oil, Mass Spectrum (APCI; Loop): m/z 541(M+H)⁺.

(g) (±)-3-(3-cyclopentyloxy-4-methoxyphenylsulfonyl)-3-(3-phenoxyphenyl)-propionic acid as a thick brown oil, Mass Spectrum (APCI; Loop): m/z 497 (M+H)⁺.

(h) (±)-3-(3-cyclopentyloxy-4-methoxyphenylsulfonyl)-3-[3-(4-methoxyphenoxy)phenyl]-propionic acid as a thick brown oil, Mass Spectrum (APCI; Loop): m/z 527(M+H)⁺.

(i) (±)-7-Benzo[1,3]dioxol-5-yl-3-(3-cyclopentyloxy-4-methoxyphenylsulfonyl)-heptanoic acid as a thick brown oil, Mass Spectrum (APCI; Loop): m/z 505(M+H)⁺.

(j) (±)-3-(4-Benzyloxyphenyl)-3-(3-cyclopentyloxy-4-methoxyphenylsulfonyl)-propionic acid as a thick brown oil, Mass Spectrum (APCI; Loop): m/z 511(M+H)⁺.

(k) (±)-3-(3-Cyclopentyloxy-4-methoxyphenylsulfonyl)-5-methyl-hexanoic acid as a thick brown oil, Mass Spectrum (APCI; Loop): m/z 385(M+H)⁺.

(l) (±)-3-(3-Cyclopentyloxy-4-methoxyphenylsulfonyl)-octanoic acid as a thick brown oil, Mass Spectrum (APCI; Loop): m/z 399(M+H)⁺.

(n) (±)-3-(3-Cyclolpentyloxy-4-methoxyphenylsulfonyl)-7-phenylheptanoic acid as a thick brown oil, Mass Spectrum (APCI; Loop): m/z 463(M+H)⁺.

(o) (±)-3-(3-Cyclopenlyloxy-4-methoxyphenylsulfonyl)-5-(4-phenoxyphenyl)-pentanoic acid as a thick brown oil, Mass Spectrum (APCI; Loop): m/z 525(M+H)⁺.

(p) (±)-5-(4-BenZyloxyphenyl)-3-(3-cyclopentyloxy-4-methoxphenylsulfonyl)-pentanoic acid as a thick brown oil, Mass Spectrum (APCI; Loop): m/z 539(M+H)⁺.

(q) (±)-3-(3-Cyclopentyloxy-4-methoxyphenylsulfonyl)-hexanoic acid as a thick brown oil, Mass Spectrum (APCI; Loop): m/z 371(M+H)⁺.

(r) (a)-3-[3-(4—Chlorophenoxy)-phenyl]-3-(3-cyclopentyloxy-4-metboxylhenylsulfonyl)-propionic acid as a thick brown oil, Mass Spectrum (APCI; Loop): m/z 531(M+H)⁺.

(s) (±)-3-(3-Cyclopentyloxy-4-methoxyphenylsulfonyl)-3-[3-(3,4-dichlorophenoxy)phenyl]-pronionic acid as a thick brown oil, Mass Spectrum (APCI; Loop): m/z 565(M+H)⁺.

(t) (±)-3-[3-(4-t-Butylphenoxy)-phenyl]-3-(3-cyclopentyloxy-4-methoxyphenylsulfonyl)-propionic acid as a thick brown oil, Mass Spectrum (APCI; Loop): m/z 552(M)⁺.

(u) (±)-3-(3-Bromo-4,5-dimethoxyphenyl)-3-(3-cyclopentyloxy-4-methoxyphenylsulfonyl)-propionic acid as a thick brown oil, Mass Spectrum (APCI; Loop): m/z 542(M+H)⁺.

(v) (±)-3-(3-Cyclopentyloxy-4-methoxyphenylsulfonyl)-3-(N-methyl-N-benzoylamino)-propionic acid as a thick brown oil, Mass Spectrum (Electrospray; loop): m/z 476 (M+H)⁺.

(w) (±)-3-(3-Cyclopenlyloxy-4-methoxyphenylsulfonyl)-4-(N-methyl-N-benzoylamino)-butanoic acid as a thick brown oil, Mass Spectrum (Electrospray; loop): m/z 490 (M+H)⁺.

(x) (±)-5-[N-methyl-N-phenylcarbamoyloxy]-3-(3-cyclolpenloxy-4-methoxyphenylsulfonyl)-pentanoic acid as a brown oil.

(y) (±)-5-(Benzyloxycarbonyl-N-methylamino)-[3-(3-cyclopenlyloxy-4-methoxyphenylsulfonyl)-pentanoic acid as a thick brown oil, Mass Spectrum (Electrospray; loop): m/z 520 (M+H)⁺.

(z) (±)-3-(3-Cyclopentyloxy-4-methoxyphenylsulfonyl)-5-(N-methyl-N-phenylcarbamoyl)-pentanoic acid as a thick brown oil, Mass Spectrum (Electrospray; loop): m/z 490 (M+H)⁺.

(aa) (±)-3-(3-Cyclopentyloxy-4-methoxy phenylsulfonyl)-6-(N-ethyl-N phenylcarbamoyl)-heptanoic acid as a thick brown oil, Mass Spectrum (Electrospray; loop): m/z 504 (M+H)⁺.

(ab) (±)-3-(3-Cyclopentyloxy-4-methoxyphenylsulfonyl)-6-(1,3-dioxo-1,3-dihydro-isoindol-2-yl)-hexanoic acid as a thick brown oil, Mass Spectrum (Electrospray; loop): m/z 516 (M+H)⁺.

(ac) (±)-3-(3-Cyclopentyloxy-4-methoxyphenylsulfonyl)-6-(3,4-dihydro-2H-guinolin-1-yl)-6-oxo-hexanoic acid as a thick brown oil, Mass Spectrum (Electrospray; loop): m/z 530 (M+H)⁺.

(ad) (±)-3-(3-Cyclopentyloxy-4-methoxyphenylsulfonyl)-5-(3,4-dihydro-2H-guinolin-1-yl)5-oxo-pentanoic acid as a thick brown oil, Mass Spectrum (Electrospray; loop): m/z 516 (M+H)⁺.

EXAMPLE 5

(±)-3-(3-Cyclopentyloxy-4-methoxyphenyl)sulfanyl-7-phenylheptanoic acid

A stirred solution of (±)-t-butyl 3-(3-cyclopentyloxy-4-methoxyphenyl)sulfanyl-7-phenylheptanoate [0.5 g, Reference Example 1(a)] in dichloromethane (20 ml), at 0° C., was treated with trifluoroacetic acid (4 ml). The solution was allowed to warm to room temperature and then stirred for 18 hours. The reaction mixture was evaporated and the brown residue subjected to flash chromatography on silica eluting with a mixture of petroleum ether and ethyl acetate (1:1, v/v) to give the title compound (0.4 g) as a colourless oil. NMR (CDCl₃): δ1.60 (m,8H), 1.90 (m,6H), 2.60 (m,4H), 3.28 (m,1H), 3.82 (s,3H), 4.74 (m,1H), 6.78 (d,1H), 7.00–7.38 (m,7H). Mass spectrum (FAB): m/z 428 M⁺.

Reference Example 1

(a) (±)-t-Butyl-3-(3-cyclopentyloxy-4-methoxyphenylsulfanyl)-7-phenylheptanoate

A stirred solution of 3-cyclopentyloxy-4-methoxybenzenethiol (0.5 g, Reference Example 2) in anhydrous tetrahydrofuran (20 ml), at 0° C. and under nitrogen, was treated with a solution of n-butyllithium in hexane (0.03 ml, 2.5M). After stirring for 15 minutes the mixture was treated dropwise with a solution of t-butyl 7-phenyl-2- heptenoate (0.39 g, Reference Example 5) in tetrahydrofuran (5 ml) and then the mixture was allowed to warm to room temperature. After stirring at room temperature for 18 hours the reaction mixture was diluted with water (50 ml) and then extracted three times with ether (30 ml). The combined organic extracts were washed with brine (50 ml), then dried over magnesium sulphate and then evaporated. The residual pale yellow oil was subjected to flash chromatography on silica eluting with a mixture of petroleum ether and ethyl acetate (97:3, v/v) to give the title compound (0.5 g) as a colourless oil. NMR (CDCl$_3$): δ1.44 (s,9H), 1.55 (m,8H), 1.95 (m,6H), 2.41 (m,2H), 2.60 (app t,2H), 3.25 (m,1H), 3.81 (s,3H) 4.74 (m,1H), 6.79 (d, 1H), 6.99 (dd,2H), 7.10–7.30 (m,5H). Mass spectrum (FAB): m/z 484 M$^+$.

Reference Example 2

3-Cyclopentyloxy-4-methoxybenzenethiol

A suspension of 3,3'-dicyclopentyloxy-4,4'-dimethoxyphenyldisulfide (15 g, Reference Example 3) and sodium borohydride (3.18 g) in anhydrous tetrahydrofuran (150 ml) at reflux was treated dropwise with anhydrous methanol (15 ml) over 1 hour. The cloudy yellow solution was stirred at reflux for 30 minutes then cooled to room temperature and stirring was continued for 18 hours. The reaction mixture was partitioned between hydrochloric acid (400 ml, 1N) and diethyl ether (400 ml). The aqueous layer was extracted three times with diethyl ether (200 ml). The combined organic phases were washed with hydrochloric acid (100 ml), then with water (100 ml) and then extracted three times with sodium hydroxide solution (200 ml, 0.2N) and once with water (200 ml). The combined aqueous extracts were acidified by addition of hydrochloric acid (1N) and then extracted five times with diethyl ether (200 ml). The combined ether extracts were washed with water (200 ml) then with brine (200 ml), then dried over magnesium sulphate and then evaporated to give the title compound (10.5 g) as a pale yellow oil. NMR (CDCl$_3$): δ1.60 (m,2H), 1.80–2.00 (m,6H), 3.40 (s,1H), 3.80 (s,3H), 4.73 (m,1 H), 6.74 (d,1H), 6.88 (dd,2H). Mass spectrum (FAB): m/z 224 (M)$^+$.

Reference Example 3

3,3'-Dicyclopentyloxy-4,4'-dimethoxyphenyldisulfide

A stirred suspension of magnesium powder (1.35 g) in anhydrous tetrahydrofuran (150 ml) heated at reflux was treated with 1,2-dibromoethane (0.32 ml). After stirring at reflux for 10 minutes the mixture was treated with a solution of 4-bromo-2-cyclopentyloxyanisole (10 g, Reference Example 4) in tetrahydrofuran (50 ml). The dark brown mixture was stirred at reflux for 1 hour then cooled to 0° C. and then added via cannula to a stirred suspension of sulfur (1.3 g) in tetrahydrofuran (50 ml). The resulting green solution was allowed to warm to room temperature. After stirring at room temperature for 18 hours the reaction mixture was partitioned between ice water (400 ml), containing concentrated hydrochloric acid (40 ml), and diethyl ether (200 ml). The aqueous phase was extracted three times with ether (200 ml). The combined organic phases were washed with hydrochloric acid (200 ml, 1N), then with water (200 ml), then with sodium hydroxide solution (200 ml, 0.1N), then with water (200 ml), then with brine (200 ml), then dried over magnesium sulphate and then evaporated. The residue was combined with the product from an additional reaction on the same scale and then subjected to gradient elution flash chromatography on silica using mixtures of petroleum ether and ethyl acetate (97:3 to 95:5 to 9:1, v/v) to give the title compound (8.8 g) as a yellow oil. NMR (CDCl$_3$): δ1.58 (m,4H), 1.74–1.95 (m,12H), 3.80 (d,6H), 4.65 (m,1H), 4.75 (m,1H), 6.70–7.12 (m,6H). Mass spectrum (FAB): m/z 446 (M)$^+$.

Reference Example 4

4-Bromo-2-cyclopentyloxyanisole

A solution of 5-bromo-2-methoxyphenol (1 g), cyclopentanol (0.54 ml) and triphenylphosphine (1.55 g) in anhydrous tetrahydrofuran (20 ml), at 0° C., was treated with diethylazodicarboxylate (0.85 mi). The resulting yellow solution was stirred at 0° C. for 40 minutes then evaporated. The residue was subjected to flash chromatography on silica eluting with a mixture of petroleum ether and ethyl acetate (19:1, v/v) to give the title compound (1.2 g) as a pale yellow oil. NMR (CDCl$_3$): δ1.62 (m,2H), 1.78–2.20 (m,6H), 3.79 (s,3H), 4.72 (m,1H), 6.70 (d,1H), 7.00 (dd,2H). Mass spectrum (FAB): m/z 270/272 (M)$^+$.

Reference Example 5

(E)t-Butyl 7-phenyl-2-heptenoate

A stirred solution of 5-phenylpentanal (9.96 g, Reference Example 6) in anhydrous tetrahydrofuran (100 ml) at room temperature was treated with (tert-butoxycarbonylmethylene)triphenylphosphorane (27.5 g). The resulting orange solution was stirred for 2.5 hours then evaporated. The residual crude product was subjected to flash chromatography on silica eluting with a mixture of hexane and ethyl acetate (19:1, v/v) to afford the title compound (12.4 g) as a colourless oil. NMR (CDCl$_3$): δ1.45 (s,9H), 1.65 (m,4H), 2.18 (q,2H), 2.61 (t,2H), 5.70 (d,1H), 6.82 (dt,1H), 7.10–7.30 (m,5H).

Reference Example 6

5-Phenylpentanal

A vigorously stirred solution of 5-phenylpentanol (10 g), sodium bromide (6.45 g) and TEMPO, 2,2,6,6-tetramethyl-1-piperidinyloxy, (0.095 g) in a mixture of ethyl acetate, toluene and water (258 ml, 7:7:1, v/v/v), at 0° C., was treated with aqueous sodium hypochlorite solution (571 ml, 0.35M) saturated with sodium bicarbonate (43.85 g) in five portions separated by 10 minute intervals. The reaction mixture was treated with ethanol (20 ml) then partitioned between water (500 ml) and ethyl acetate (500 ml). The aqueous layer was extracted twice with ethyl acetate (500 ml). The combined organic phases were washed with aqueous sodium thiosulphate (500 ml, 5%), then with water (200 ml), then with brine (200 ml), then dried over magnesium sulphate and then evaporated to give the title compound as an orange oil, which was used without further purification. NMR (CDCl$_3$): δ1.65 (m,4H), 2.35 (m,2H), 2.60 (t,2H), 7.10–7.30 (m,5H), 9.75 (s,1H).

(b) By proceeding in a manner similar to Example 1(a) but using (±)-3-(4-cyclopentyloxy-3-methoxyphenylsulfanyl)-7-phenylheptanohydroxamic acid there was prepared (±)-3-(4-cyclopentyloxy-3-methoxnphenylsulfonyl)-7-phenylheptanohydroxamic acid as a white solid, m.p. 146–147° C. NMR [(CD$_3$)$_2$SO]: 8 1.20–2.00 (m,14H), 2.10 (m,2H), 2.42 (m,2H), 3.45 (m,1H), 4.90 (m,1H), 7.03–7.23 (m,7H), 7.32 (dd, 1H), 8.85 (s,1H), 10.55 (s,1H). Mass spectrum (FAB):

m/z 476 (M+H)+. [Elemental analysis: C,63.18; H,6.76; N,2.69%. Calculated for $C_{25}H_{33}NO_6S$:- C,63.14; H,6.99; N,2.95%].

(b) By proceeding in a manner similar to Example 3(a) but using (±)-3-(4-cyclopentyloxy-3-methoxyphenyl) sulfanyl-7-phenylheptanoic acid there was prepared (±)-3-(4-cyclopentyloxy-3-methoxyphenyl)sulfanyl-7-phenylheptanohydroxamic acid as a white foam. NMR ($CDCl_3$): δ1.60 (m,8H), 1.90 (m,6H), 2.34 (br d,1H), 2.60 (br t,2H), 2.88 (d,1H), 3.32 (m,1H), 3.80 (s,3H), 4.74 (m,1H), 6.76 (d,1H), 6.94 (dd,2H), 7.10–7.30 (m,5H). Mass spectrum (ISp): 444 (M+H)+.

(b) By proceeding in a similar manner to Example 5(a) but using (±)-t-butyl-3-(4-cyclopentyloxy-3-methoxyphenyl) sulfanyl-7-phenylheptanoate there was prepared (±)-3-(4-cyclopentyloxy-3-methoxyphenyl)sulfonyl-7-phenylheptanoic acid as a pale yellow oil. NMR ($CDCl_3$): δ1.64 (m,8H), 1.90 (m,6H), 2.60 (m,4H), 3.30 (br t,1H), 3.80 (s,3H), 4.73 (m,1H), 5.05 (br s,1H), 6.80 (d,1H), 7.0 (dd,2H), 7.12–7.30 (m,5H). Mass spectrum (FAB): m/z 429 (M+H)+.

In Vitro and In Vivo Test Procedures 1. (a) Inhibitory Effects of Compounds on PDE IV Activity 1.1 Preparation of PDE From Guinea Pig Macrophages The method is described in Turner et al. (Br. J. Pharmacol, 108, 876–883, 1993). Briefly, cells are harvested from the peritoneal cavity of horse-serum treated (0.5 ml i.p.) Dunkin Hartley guinea pigs (250–400 g) and the macrophages purified by discontinuous (55%, 65%, 70% v/v) gradient (Percoll) centrifugation. Washed macrophages are plated out in cell culture flasks and allowed to adhere. The cells are washed with Hank's balanced salt solution, scraped from the flasks and centrifuged (1000 g). The supernatant is removed and the pellets stored at −80° C. until use. The pellet is homogenised in 20 mM tris(hydroxymethyl)aminomethane HCl, pH7.5, 2 mM magnesium chloride, 1 mM dithiothreitol, 5 mM ethylenediaminetetraacetic acid, 0.25 mM sucrose, 20 mM p-tosyl-L-lycine chloromethyl ketone, 10 mg/ml leupeptin and 2000U/ml aprotinin.

1.2 Measurement of PDE Activity

PDE activity is determined in macrophage homogenates by the two-step radioisotopic method of Thompson et al., (Adv. Cyclic Nucl. Res., 10 69–92, 1979). The reaction mixture contains 20 mM tris(hydroxymethyl)aminomethane HCl (pH8.0), 10 mM magnesium chloride, 4 mM 2-mercaptoethanol, 0.2 mM ethylenebis(oxyethylenenitrilo) tetraacetic acid and 0.05 mg of bovine serum albumin/mL. The concentration of substrate is 1 μM. The $IC_{50}$ values (i.e. concentrations which produce 50% inhibition of substrate hydrolysis) for the compounds examined are determined from concentration-response curves in which concentrations range from 0.01 nM to 40 μM.

(b) Inhibitory Effects of Compounds on PDE V Activity 1.3 Preparation of PDE from Human Platelets The method is described in R. E. Weishaar et al. (Biochem.Pharmacol.,35 787–800, 1986).

1.4 Measurement of PDE Activity

PDE activity is determined by the radioisotopic method of Thompson et al., (Adv. Cyclic Nucl. Res., 10 69–92, 1979). Following incubation for 30 minutes at 30° C. [$^3$H]-Guanosine 5'-monophosphate is separated from the substrate, guanosine [$^3$H]-guanosine 3':5'-cyclic monophosphate, by elution on cation-exchange columns, and radioactivity is determined using a liquid scintillation counter (LS 1701, Beckman) using a liquid scintillation cocktail (Flow Scint III, Packard). The concentration of substrate is 1 μM. The $IC_{50}$ values (i.e. concentrations which produce 50% inhibition of substrate hydrolysis) for the compounds examined are determined from concentration-response curves in which concentrations range from $10^{-11}$ M to $10^{-5}$M.

2. In Vivo Bronchodilator Actions of Compounds 2.1 Measurement of Bronchodilatation Bronchorelaxant activity is measured in in vivo tests in the anaesthetized guinea-pig or rat according to the method described in Underwood et al., Pulm. Pharmacol. 5, 203–212, (1992) in which the effects on bronchospasm induced by histamine (or other spasmogens such as methacholine or leukotriene $D_4$) is determined. Compounds are administered orally 1 hour prior to administration of spasmogen.

3. In Vivo Actions of Compounds on Antigen (Ovalbamin)-induced Eosinophilia in Guinea-pigs 3.1 Treatment of Animals and Measurement of Eosinophil Numbers Male Dunkin-Hartley guinea-pigs weighing 200–250 g are sensitized using 10 μg ovalbumin in 1 mL of a 100 mg/mL suspension of aluminium hydroxide, i.p.

28 days after sensitization guinea-pigs are dosed orally. 23 Hours later this procedure is repeated and 60 minutes later the guinea-pigs are challenged with nebulised saline or ovalbumin (1% in saline) for 15 seconds. 24 Hours after challenge the guinea-pigs are killed and the lungs are lavaged with warm saline. Total and differential cell counts are made.

4. Inhibitory Effects of Compounds Against Antigen-induced Eosinophilia in the Rat In Vivo 4.1. Treatment of Rats and Measurement of Eosinophil Numbers Male Brown Norway rats weighing 150–250 g are sensitized on days 0, 12 and 21 with ovalbumin (100 μg, i.p.). Rats are challenged on any one day between days 27–32. 24 hours and 1 hour before antigen challenge rats are dosed orally. Rats are challenged by exposure for 30 minutes to nebulized saline or ovalbumin (1% in saline). 24 hours after challenge, rats are killed and the airways are lavaged with physiological salt solution. Total and differential cell counts are made.

5. In Vitro Inhibitory Effects on TNF-alpha Release by Human Monocytes

The effects of compounds on TNF-alpha production by human peripheral blood monocytes (PBMs) are examined as follows.

5.1. Preparation of Blood Leukocytes

Blood is drawn from normal donors, mixed with dextran, and the erythrocytes allowed to sediment for 35 minutes at 37° C. Leukocytes are fractionated by centrifugation through a discontinuous (18, 20 and 22%) metrizamide gradient. The mononuclear cell fraction comprising 30–40% PBMs is suspended in Hank's balanced salt solution and stored at 4° C. until use.

5.2. Measurement of TNF-alpha

Cells from the PBM-rich metrizamide fraction are spun down (200 g for 10 minutes at 20° C.), resuspended at $10^6$PBMs/mL of medium; RPMI 1640 containing 1%v/v FCS, 50U/mL penicillin and 50 mg/mL streptomycin (Gibco, U.K.), then plated out in 96 well plates at $2\times10^5$ cells/well. The medium (200 μL) is changed to remove any non-adherent cells and the remaining, adherent PBMs left in the incubator overnight (18 hours). One hour prior to challenge, the medium is changed to that containing compound for test or drug vehicle. Control treatments and compounds for test are assayed in quadruplicate wells. Compounds are tested within the concentration range of $3\times10^{-11}$M to $3\times10^{-6}$M. Medium (50 μL) with or without long/mi LPS (*E. coli,* 055 B5 from Sigma, U.K.) is then added. The incubation is then continued for a further 4 hours. Cell supernatants are removed for storage at −20° C.

TNF-alpha levels in cell supernatants are quantified using a standard sandwich ELISA technique. ELISA plates (Costar, U.K.) are coated overnight at 4° C. with 3 mg/mL polyclonal goat anti-human TNF-alpha antibody (British Biotechnology, U.K.) in pH9.9 bicarbonate buffer. Rabbit polyclonal anti-human TNF-alpha antiserum (Janssen Biochimicha, Belgium) at 1/500 dilution is used as the second antibody and polyclonal goat anti-rabbit IgG horseradish peroxidase (Calbiochem, U.S.A.) at 1/8000 dilution is used as the detection antibody. Color development is measured by absorbance at 450 nm using a Titek plate reader.

TNF-alpha levels are calculated by interpolation from a standard curve using recombinant human TNF-alpha (British Biotechnology U.K.)(0.125–8 ng/mL). Data (log-conc. vs. log-resp) are fitted by linear regression (p>0.99) using a Multicalc (Wallac Pharmacia, U.K.) software program. Basal TNF-alpha levels are less than 100 pg/mL whilst LPS (lipopoly-saccharide) stimulation of the PBMs increases TNF-alpha levels to 3–10 ng/mL.

5.3. Results

Compounds within the scope of the invention produce 50% inhibition of LPS induced TNF-alpha release from human monocytes at concentrations from about 0.01 nM to about 1 μM.

6. Inhibitory Effects of Compounds on Antigen-induced Bronchoconstriction in the Conscious Guinea-pig 6.1 Sensitisation of Guinea-pigs and Measurement of Antigen-induced Bronchoconstriction Male Dunkin-Hartley guinea-pigs (550–700 g) are sensitized as above. Specific airways resistance (SRaw) is measured in conscious animals by whole body plethysmography using a variation of the method of Pennock et al., (*J. Appl. Physiol.,* 46 399, 1979). Test compounds or vehicle are administered orally 24 hours and 1 hour before antigen challenge. 30 Minutes before challenge the animals are injected with mepyramine (30 mg/kg i.p.) to prevent anaphyl-actic collapse and placed into the plethysmography chambers where SRaw is determined at 1 minute intervals. Resting SRaw is then determined. Animals are challenged with an aerosol of ovalbumin and SRaw is determined every 5 minutes for 15 minutes.

7. Inhibitory Effects of Compounds Against Antigen-induced Bronchoconstriction in the Anaesthetized Rat In Vivo 7.1. Treatment of Rats and Measurement of Antigen-induced Bronchoconstriction Male Brown Norway rats weighing 150–250 g are sensitized on days 0, 12 and 21 with ovalbumin (100 μg, i.p.). Rats are challenged on any one day between days 27–32. 24 hours and 1 hour before antigen challenge rats are dosed orally. Rats are anaesthetized to allow recording of lung function (airway resistance and lung compliance) using respiratory mechanics software. Rats are challenged with ovalbumin i.v. and the peak changes in airway resistance and lung compliance are determined.

8. Inhibitory Effects of Compounds on Serum TNF-alpha Levels in LPS-challenged Mice 8.1. Treatment of Animals and Measurement of Murine TNF-alpha Female Balb/c mice (age 6–8 weeks, weight 20–22 g from Charles River, U.K.) in groups of five or more animals are dosed p.o. with compounds suspended in 1.5% (w/v) carboxymethyl cellulose then challenged after a minimum period of 30 minutes with 30 mg of LPS i.p. After 90 minutes the animals are killed by carbon dioxide asphyxiation and bled by cardiac puncture. Blood is allowed to clot at 4° C., centrifuged (12,000 g for 5 minutes) and serum taken for TNF-alpha analysis. TNF-alpha levels are measured using a commercially available murine TNF-alpha ELISA kit, purchased from Genzyme (Cat. no. 1509.00), as recommended by the manufacturer. Values for TNF-alpha are calculated from a recombinant murine TNF-alpha standard curve.

9. Systemic Bioavailability in Female Balb/c Mouse

Intravenous Administration

Following surgery to expose the jugular vein for dosing, a solution of test compound in dimethylsulphoxide is added at a dose of 1 mg/kg body weight.

Oral Administration

A suspension of test compound in 1.5% aqueous carboxymethylcellulose is introduced into the stomach by gavage at a dose of 1 mg/kg body weight. Following either i.v. or oral dosing, blood is obtained by cardiac puncture following carbon dioxide asphyxiation and is obtained at a single time post-dose for each animal. Three animals are sacrificed at each time point. Blood samples are obtained at the following times after dosing by both the i.v. and oral routes; 5 minutes (i.v. only), 0.25, 0.5, 1, 2, 3, 4, 5.5, 7 and 24 hours. Corresponding plasma is obtained by centrifugation of each blood sample. The drug content in the plasma samples is then determined using conventional methods.

9.1 Metabolism (i)Preparation of Mouse Liver Homogenate

Fresh mouse liver is homogenised in sucrose-phosphate buffer. Following centrifugation the resulting supernatant (liver homogenate) is used fresh or frozen in liquid nitrogen for one minute and stored at −30° C. to −40° C. prior to use.

(ii) Incubation of Compounds with Mouse Liver Homogenate

To 0.5 ml of mouse liver homogenate is added 0.5 ml taken from a vortexed mixture of 8 mg NADPH added to a mixture of aqueous magnesium chloride (1 ml, 0.1 5M) nicotinamide (1 ml, 0.5M) and pH 7.4 tris buffer (8.5 ml, 0.1M). The compound is added at a concentration of 1 mg/ml in 10 ml of solvent. Incubates are maintained at 37° C. Samples are taken at 0 minutes, 5 minutes, 10 minutes, 20 minutes and 30 min and the incubation stopped by the addition of 100 ml acetonitrile. The drug content in the incubation samples is determined using conventional methods.

10. Streptococcal Cell Wall-Induced Arthritis in Rats 10.1 Preparation of *S. pyogenes* Purified Cell Wall Purified *S. pyogenes* cell wall is prepared from the cell pellet of a log-phase culture of *S. pyogenes,* group A, strain D-58. The whole bacteria are homogenized by grinding with glass beads and the crude cell wall collected by centrifugation and subsequently washed with 2% sodium dodecyl sulphate in phosphate buffered saline followed by phosphate buffered saline to remove contaminating proteins and nucleic acids. The cell wall is further purified by sonication and differential centrifugation to obtain a purified preparation which pelleted at 100,000 g. This material is suspended in sterile phosphate buffered saline and the quantity of cell wall determined by measuring the rhamnose content of the preparation (purified cell wall contains 28% rhamnose by weight). The material is filtered through a 0.22 mM filter and stored at 4° C. until used for arthritis induction.

10.2 Arthritis Induction and Measurement of Joint Diameters

Female Lewis rats weighing 140–160 g are injected intra-articularly into the left or right tibio-tarsal joint on day

What is claimed is:

1. A compound of general formula (I):

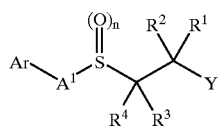

wherein

R$^1$ and R$^3$ may be the same or different and each independently represents a group —L$^1$—R$^5$, where L$^1$ is a direct bond, a straight or branched C$_{1-6}$alkylene chain, a straight or branched C$_{2-6}$alkenylene chain, a straight or branched C$_{2-6}$alkylylene chain or a straight or branched C$_{1-6}$alkylene chain containing an oxygen or sulfur atom, a phenylene, imino (—NH—) or alkylimino linkage, or a sulfinyl or sulfonyl group, in which each of the alkylene, alkenylene and alkynylene chains may be optionally substituted, the substituents selected from alkoxy, aryl, carboxy, cyano, cycloalkyl, halogen, heteroaryl, hydroxyl, or oxo; and R$^5$ represents hydrogen, aryl, aroyl, carboxy or an acid bioisostere, cyano, cycloalkyl, cycloalkenyl, heterocyceloalkyl, heteroaryl, arylalkoxycarbonyl, —NH—C(=O)—NH$_2$, —C=N—O—C(=O)—NH$_2$, —C=(O)—NY$^1$Y$^2$, (where Y$^1$ and Y$^2$ are independently selected from hydrogen, alkyl, arylalkyl, and aryl, or the group NY$^1$Y$^2$ may form a 4–6 membered cyclic amine {which may optionally contain a further heteroatom selected from O, S, or NR$^6$ in which R$^6$ is hydrogen, alkyl, aryl or arylalkyl, or which may be fused to an additional aromatic ring}), —NY$^1$SO$_2$aryl, —NHR$^6$, —SR$^6$, or —OR$^6$;

R$^2$ and R$^4$ may be the same or different and are each independently hydrogen or alkyl; or R$^2$ and R$^4$ together form a bond; or R$^1$ and R$^2$, or R$^1$ and R$^3$, or R$^3$ and R$^4$ together with the carbon atom(s) to which they are attached form a 3 to 8 membered cycloalkyl or cycloalkenyl ring, optionally substituted by alkyl, arylalkyl, or heteroarylalkyl, and which may optionally contain a heteroatom selected from O, S or NR$^6$; or R$^1$ and R$^3$ together with the carbon atoms to which they are attached form a heteroaryl ring;

Y represents carboxy or an acid bioisostere;

A$^1$ represents a direct bond, a straight or branched C$_{1-4}$alkylene chain or a NR$^6$ group;

Ar is a group selected from:

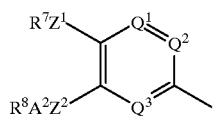

and

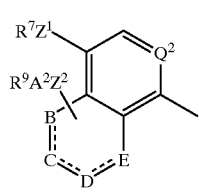

where the dotted lines indicate optional bonds between B—C, and/or C—D, and/or D—E;

R$^7$ represents a straight- or branched-chain alkyl group of 1 to about 6 carbon atoms, optionally substituted by one or more halogen atoms, or when Z$^1$ represents a direct bond R$^7$ may also represent a hydrogen atom or a lower alkenyl or lower alkynyl group;

R$^8$ represents an optionally substituted cycloalkyl, cycloalkenyl, heterocycloalkyl, aryl, heteroaryl or partially saturated bicycloaryl group;

R$^9$ represents R$^{10}$, —OR$^{10}$, —SR$^{10}$, —SOR$^{12}$, —SO$_2$R$^{12}$, —SO$_2$NR$^{10}$R$^{11}$, —NR$^{10}$SO$_2$R$^{12}$, —NR$^{10}$R$^{11}$, —O(C—O)NR$^{10}$R$^{11}$, —NR$^{10}$C(=O)R$^{12}$, —N(OH)C(=O)R$^{12}$, or —C(=O)N(OH)R$^{12}$ (where R$^{10}$ and R$^{11}$, which may be the same or different, each represent a hydrogen atom, or an alkyl, alkenyl, heterocycloalkyl, cycloalkyl, cycloalkenyl, aryl, heteroaryl, arylalkyl or heteroarylalkyl group, or the group NR$^{10}$R$^{11}$ may also represents a 3 to 7 membered cyclic amine optionally containing one or more additional heteroatom selected from O, NR$^6$, or S, and R$^{12}$ represents an alkyl, alkenyl, heterocycloalkyl, cycloalkyl, cycloalkenyl, aryl, heteroaryl, arylalkyl or heteroarylalkyl group);

A$^2$ represents a direct bond; and Z$^2$ represents an oxygen or sulfur atom; or A$^2$ represents a straight- or branched C$_{1-6}$alkylene chain optionally substituted by halogen, hydroxyl, alkoxy, oxo, cycloalkyl, aryl or heteroaryl; and Z$^2$ represents an oxygen or sulfur atom or a direct bond; or A$^2$ represents a straight- or branched-carbon chain comprising from 2 to about 6 carbon atoms which contains a double or triple carbon-carbon bond, or is interrupted by an oxygen or sulfur atom, a phenylene, imino (—NH—) or alkylimino linkage, or a sulfinyl or sulfonyl group; and Z$^2$ represents an oxygen or sulfur atom or a direct bond;

B, C, D, and E independently represent a carbon atom or a heteroatom selected from O, S, N, NOR$^{13}$ or NR$^{13}$ (where R$^{13}$ is hydrogen or a C$_{1-4}$straight- or branched-chain alkyl, aryl, arylC$_{1-4}$alkyl, heteroaryl or heteroarylC$_{1-4}$alkyl group), or three of B, C, D or E represent a carbon atom or a heteroatom as defined above and the other represents a direct bond; but excluding compounds where two O or S atoms are in adjacent positions;

Q$^1$, Q$^2$ and Q$^3$, which may be the same or different, each represents a CH or CX$^1$ linkage or a nitrogen atom (where X$^1$ represents a halogen atom); and n is 0, 1 or 2, (with the proviso that when $A^1$ is $NR^6$ n is 2);

and N-oxides thereof, and their prodrugs, pharmaceutically acceptable salts, and solvates (e.g. hydrates), thereof, but excluding the compound 3-[3-(4-fluorophenyl)phenylthio]propionic acid.

2. A compound according to claim 1 in which $R^1$ represents a group $R^5$ wherein $R^5$ is hydrogen, $NHR^6$ or $OR^6$.

3. A compound according to claim 2 in which $R^6$ is hydrogen.

4. A compound according to claim 1 in which $R^1$ represents a group —$L^1$—$R^5$ where $L^1$ is a straight or branched $C_{1-6}$alkylene chain and $R^5$ is hydrogen or $SR^6$.

5. A compound according to claim 1 in which $R^1$ represents hydrogen.

6. A compound according to claim 1 in which $R^2$ represents hydrogen or alkyl.

7. A compound according to claim 6 in which $R^2$ represents hydrogen.

8. A compound according to claim 1 in which $R^3$ represents a group —$L^1$—$R^5$ where $L^1$ is a straight or branched $C_{1-6}$alkylene chain and $R^5$ is hydrogen, aryl, heteroaryl, —C(=O)—$NY^1Y^2$ (where $Y^1$ and $Y^2$ are as defined in claim 1) or heterocycloalkyl.

9. A compound according claim 1 in which $R^3$ represents a group —$L^1$—$R^5$ where $L^1$ is a straight or branched $C_{1-6}$alkylene chain which contains an alkylimino linkage and $R^5$ is an arylalkyl ester of a carboxy group.

10. A compound according to claim 1 in which $R^3$ represents a group —$L^1$—$R^5$ where $L^1$ is a straight or branched $C_{1-6}$alkylene chain which contains an oxygen and $R^5$ is a group —C(=O)$NY^1Y^2$ (where $Y^1$ and $Y^2$ are as defined in claim 1).

11. A compound according to claim 1 in which $R^3$ represents a group —$L^1$—$R^5$ where $L^1$ is a direct bond and $R^5$ is aryloxyaryl, aryl, heteroaryl, arylalkyloxyaryl or heteroarylalkyloxyaryl.

12. A compound according to claim 1 in which $R^4$ represents hydrogen or alkyl.

13. A compound according to claim 12 in which $R^4$ represents hyd rogen.

14. A compound according to claim 1 in which Y represents a —C(=O)NHOH group.

15. A compound according to claim 1 in which $A^1$ represents a direct bond.

16. A compound according to claim 1 in which Ar represents a group (i) as defined in claim 1.

17. A compound according to claim 1 in which Ar represents a group (ii) as defined in claim 1.

18. A compound of formula (Ia)

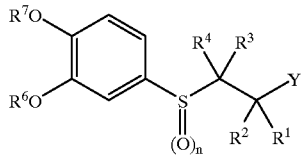

(Ia)

wherein $R^1$, $R^2$, $R^3$, $R^4$, $R^7$, $R^8$, and n are as defined in claim 1 and Y is a —C(=O)NHOH group, N-oxides thereof and their prodrugs, pharmaceutically acceptable salts, and solvates thereof.

19. A compound according to claim 18 in which $R^7$ is methyl and $R^8$ is cyclopentyl.

20. A compound according to claim 18 in which n is 2.

21. A compound according to claim 18 in which $R^2$ and $R^4$ represent hydrogen.

22. A compound according to claim 18 in which $R^1$ represents hydrogen.

23. A compound according to claim 18 in which $R^3$ represents a group —$L^1R^5$ where $L^1$ is a straight or branched $C_{1-6}$alkylene chain and $R^5$ is hydrogen, aryl, heteroaryl, —C(=O)—$NY^1Y^2$ (where $Y^1$ and $Y^2$ are as defined in claim 18 or heterocycloalkyl.

24. A compound selected from the group consisting of:
3-(3-cyclopentyloxy-4-methoxyphenylsulfonyl)-7-phenylheptanohydroxamic acid;
3-(3-cyclopentyloxy-4-methoxyphenylsulfonyl)-5-phenylpentanohydroxamic acid;
3-(3-Cyclopentyloxy-4-methoxyphenylsulfonyl)-3-(thiophen-3-yl)-propionohydroxamic acid;
5-(4-butoxyphenyl)-3-(3-cyclopentyloxy-4-methoxyphonylsulfonyl)-pentanohydroxamic acid;
3-(3-benzyoxyphenyl)-3-(3-cyclopentyloxy-4-methoxyphenylsulfonyl)-propionohydroxamic acid;
3-(2-benzyloxyphenyl)3-(3-cyclopentyloxy-4-methoxyphenylsulfonyl)-propionohydroxamic acid;
3-(3-benzyloxy-4-methoxyphenyl)-3-(3-cyclopentyloxy-4-methoxyphenylsulfonyl)-propionohydroxamic acid;
3-(3-cyclopentyloxy-4-methoxyphenylsulfonyl)-3-(3-phenoxyphenyl)-propionohydroxamic acid;
3-(3-cyclopentyloxy-4-methoxyphenylsulfonyl)-3-[3-(4-methoxyphenoxy)phenyl]-propionohydroxamic acid;
7-(benzo[1,3]dioxol-5-yl)-3-(3-cyclopentyloxy-4-methoxyphenylsulfonyl)-heptanohydroxamic acid;
3-(4-benzyloxyphenyl)-3-(3-cyclopentyloxy-4-methoxy phenylsulfonyl)-propionohydroxamic acid;
3-(3-cyclopentyloxy-4-methoxyphenylsulfonyl)-5-methylhexanohydroxamic acid;
3-(3-cyclopentyloxy-4-methoxyphenylsufonyl)-octanohydroxamic acid;
3-(3-cyclopentyloxy-4-methoxyphenylsulfonyl)-7-phenylheptanohydroxamic acid;
3-(3-cyclopentyloxy-4-methoxyphenylsufonyl)-5-(4-phenoxyphenyl)-pentanohydroxamic acid;
5-(4-benzyloxyphenyl)-3-(3-cyclopentyloxy-4-methoxyphenylsulfonyl)-pentanohydroxamic acid;
3-(3-cyclopentyloxy-4-methoxyphonylsufonyl)-hexanohydroxamic acid;
3-[3-(4-chlorophenoxy)phenyl]-3-(3-cyclopentyloxy-4-methoxyphenylsufonyl)-propionohydroxamic acid;
3-(3-cyclopentyloxy-4-methoxyphenylsulfonyl)-3-[3-(3,4-dichlorophenoxy)phenyl]-propionohydroxamic acid;
3-(3-(4-t-butyl-phenoxy)phenyl]-3-(3-cyclopentloxy-4-methoxyphenylsulfonyl)-propionohydroxamic acid;
3-(3-bromo-4,5-dimethoxyphenyl)-3-(3-cyclopentyloxy-4-methoxyphenylsufonyl)-butyrohydroxamic acid;
3-(3-cyclopentyloxy-4-methoxyphenylsulfonyl)-4-(N-methyl-N-benzoylamino)-pentanohydroxamic acid;
3-(3-cyclopentyloxy-4-methoxyphenylsulfonyl)-5-(N-methyl-N-benzoylamino)-butyrohydroxamic acid;
3-(3-cyclopentyloxy-4-methoxyphenylsulfonyl)-5-(N-methyl-N-phenylcarbamoyloxy)-pentanohydroxamic acid;
5-(benzyloxycarbonyl-N-methylamino)-3-(3-cyclopentyloxy-4-methoxyphenylsulfonyl)-pentanohydroxamic acid;
3-(3-cyclopentyloxy-4-methoxyphenylsulfonyl)-5-(N-methyl-N-phenylcarbamoyl)-pentanohydroxamic acid;
3-(3-cyclopentyloxy-4-methoxyphenylsulfonyl)-6-(N-methyl-N-phenylcarbamoyl)-hexanohydroxyamic acid;
3-(3-cyclopentyloxy-4-methoxyphenylsulfonyl)-6-1,3-dioxo-1,3-dihydro-isoindol-2-yl)-hexanohydroxamic acid;

3-(3-cyclopentyloxy-4-methoxyphenylsulfonyl)6-(3,4-dihydro-2H-quinolin-1-yl)-7-oxo-hexanohydroxamic acid;

3-(3-cyclopentyloxy-4-methoxyphenylsulfonyl)-5-(3,4-dihydro-2H-quinolin-1-yl)-oxo-pentanohydroxamic acid;

3-(3-cyclopentyloxy-4-methoxyphenyl)sulfanyl-7-phenylheptanohydroxamic acid;

3-(7-methoxy-2-methoxymethyl-3H-benzimidazol-4-yl)sulfonyl-7-phenylheptanohydroxamic acid;

3-(7-methoxy-2-cyclopropyl-3H-benzimidazol-4-yl)sulfonyl-7-phenylheptanohydroxamic acid;

3-(7-methoxy-2-methoxymethyl-3H-benzimidazol-4-ylsulfonyl)-7-phenylheptanohydroxamic acid;

3-(7-methoxy-2-cyclopropyl-3H-benzimidazol-ylsulfonyl)-7-phenylheptanohydroxamic acid;

3-(4 methoxy-3-[trans-3-phenoxy-cyclopentyloxy]phenylsulphonyl)-7-phenylheptanohydroxamic acid;

3-(4-methoxy-3-[trans-3-(pyridin-2-yloxy)-cyclopentyloxy]phenylsulphonyl)-7-phenylheptanohydroxamic acid;

3-(4-methoxy-3-[trans-3-(pyridin-3-yloxy)-cyclopentyloxy]phenylsulphonyl)-7-phenylheptanohydroxamic acid;

3-(4-methoxy-3-[trans-3-(pyridin-4-yloxy)-cyclopentyloxy]phenylsulphonyl)-7-phenylheptanohydroxamic acid;

3-(4-methoxy-3-[cis-3-(pyridin-2-yloxy)-cyclopentyloxy]phenylsulphonyl)-7-phenylheptanohydroxamic acid;

3-(4-methoxy-3-[cis-3-(pyridin-3-yloxy)-cyclopentyloxy]phenylsulphonyl)-7-phenylheptanohydroxamic acid;

3-(3-[N-t-butoxycarbonylpyrrolidin-3-yloxy]-4-methoxyphenylsulphonyl)-7-pbenylheptanohydroxamic acid;

3-(4-methoxy-3-[(N-phenyl)pyrrolidin-3-yloxy]phenysulphonyl)-7-phenylheptanohydroxamic acid;

3-(4-methoxy-3(2-phenyl-ethoxy)phenylsulphonyl)-7-phenylheptanohydroxamic acid;

3-(4-methoxy-3-(4-phenyl-butoxy)phenylsulphonyl)-7-phenylheptanohydroxamic acid;

3-(4-difluoromethoxy-3-[2-phenyloxy]phenylsulphonyl)-7-phenylheptanohydroxamic acid;

3-(4-methoxy-3-(2-benzyloxyethoxy)phenylsulphonyl)-7-phenylheptanohydroxamic acid;

3-(4-methoxy-3-(2-phenoxyethoxy)phenylsulphonyl)-7-phenylheptanohydroxamic acid;

3-(5-methoxy-4-[2-(4-methoxyphenyl)ethoxy]pyridin-2-ylsulphonyl)-7-phenylheptanohydroxamic acid;

3-(4-methoxy-3-(2-indanyloxy)phenylsulphonyl)-7-phenylheptanohydroxamic acid;

3-(4-methoxy-3-[2-(pyridin-2-yl)ethoxy]phenylsulphonyl)-7-phenylheptanohydroxamic acid;

3-(4-methoxy-3-[3-(pyridin-4-yl)propyloxy]phenylsulplonyl)-7-phenylheptanohydroxamic acid;

3-(4-methoxy-3-[3-(pyridin-3-yl)propyloxy]phenylsulphonyl)-7-phenylheptanohydroxamic acid;

3-(5-methoxy-4-[2-(pyridin-2-yl)ethoxy]pyridin-2-ylsulphonyl)-7-phenylheptanohydroxamic acid;

3-(4-methoxy-3-(2-thien-2-ylethoxy)phenylsulphonyl)-7-phenylheptanohydroxamic acid;

3-(3-{3-(4-chloropbenyl)-1,2,4-oxadiazol-5-ylmethoxy}-4-methoxyphenylsulphonyl)-7-phenylheptanohydroxamic acid;

3-(3-{3-(4-methoxyphenyl)-1,2,4-oxadiazol-5-ylmethoxy}-4-methoxyphenylsulphonyl)-7-phenylheptanohydroxamic acid;

3-(3-[3-(pyridin-2-yl)-1,2,4-oxadiazol-5-ylmethoxy]-4-methoxyphenylsulphonyl)-7-phenylheptanohydroxamic acid;

3-(3-[2-(4-chlorophenyl)-1,3,4-oxadiazol-5-ylmethoxy]-4-methoxyphenylsulphonyl)-7-phenylheptanohydroxamic acid;

3-(3-cyclopentyloxy-4-methoxyphenylsulfonyl)-5-phenylpentanoic acid;

3-(3-cyclopentyloxy-4-methoxyphenylsulfonyl)-3-(thiophen-3-yl)-propionic acid;

5(4-butoxyphenyl)-3-(3-cyclopentyloxy-4-methoxyphenylsulfonyl)-pentanoic acid;

3-(3-benzyloxyphenyl)-3-(3-cyclopentyloxy-4-methoxyphenylsulfonyl)-propionic acid;

3-(2-benzyloxyphenyl)-3-(3-cyclopentyloxy-4-methoxyphenylsulfonyl)-propionic acid;

3-(3-benzyloxy-4-methoxyphenyl)-3-(3-cyclopentyloxy-4-methoxyphenylsulfonyl)-propionic acid;

3-(3-cyclopentyloxy-4-methoxyphenylsulfonyl)-3-(3-phenoxyphenyl)-propionic acid;

3-(3-cyclopentyloxy-4-methoxyphenylsulfonyl)-3-[3-(4-methoxyphenoxy)phenyl]-propionic acid;

7-benzo[1,3]dioxol-5-yl-3-(3-cyclopentyloxy-4-methoxyphenylsulfonyl)-heptanoic acid;

3-(4-benzyloxyphenyl)-3-(3-cyclopentloxy-4-methoxyphenylsulfonyl)-propionic acid;

3-(3-cyclopentyloxy-4-methoxy-phenylsulfonyl)-5-methyl-hexanoic acid;

3-(3-cyclopentyloxy-4-methoxy-phenylsulfonyl)-octanoic acid;

3-(3-cyclopentyloxy-4-methoxy-phenylsulfonyl)-7-phenylheptanoic acid;

3-(3-cyclopentyloxy-4-methoxy-phenylsulfonyl)-5-(4-phenoxyphenyl)-pentanoic acid;

5-(4-benzyloxyphenyl)-3-(3-cyclopentyloxy-4-methoxy-phenylsulfonyl)-pentanoic acid;

3-(3-cyclopentyloxy-4-methoxyphenylsulfonyl)-hexanoic acid;

3-[3-(4-chlorophenoxy)-phenyl]-3-(3-cyclopentyloxy-4-methoxyphenylsulfonyl)-propionic acid;

3-(3-cyclopentyloxy-4-methoxy-phenylsulfonyl)-3-[3-(3,4-dichlorophenoxy)phenyl]-propionic acid;

3-[3-(4-t-butylphenoxy)-phenyl]-3-(3-cyclopentyloxy-4-methoxyphenylsulfonyl)-propionic acid;

3-(3-bromo-4,5-dimethoxyphenyl)-3-(3-cyclopentyloxy-4-methoxyphenylsulfonyl)-propionic acid;

3-(3-cyclopentyloxy-4-methoxyphenylsulfonyl)-3-(N-methyl-N-benzoyamino)-butanoic acid;

3-(3-cyclopentyloxy-4-methoxyphenylsulfonyl)-4-(N-methyl-N-benzoylamino)-pentanoic acid;

5-[N-methyl-N-phenylcarbamoyloxy]-3-(3-cyclopentyloxy-4-methoxyphenylsulfonyl)-pentanoic acid;

5-(benzyloxycarbonyl-N-methylamino)-[3-(3-cyclopentyloxy-4-methoxyphenylsulfonyl)-pentanoic acid;

3-(3-cyclopentyloxy-4-methoxyphenylsulfonyl)-5-(N-methyl-N-phenylcarbamoyl)-pentanoic acid;

3-(3-cyclopentyloxy-4-methoxyphenylsulfonyl)-6-(N-ethyl-Nphenylcarbamoyl)-heptanoic acid;

3-(3-cyclopentyloxy-4-methoxyphenylsulfonyl)-6-(1,3-dioxo-1,3-dihydro-isoindol-2-yl)-hexanoic acid;

3-(3-cyclopentyloxy-4-methoxyphenylsulfonyl)-6-(3,4-dihydro-2H-quinolin-1-yl)-6-oxo-hexanoic acid;

3-(3-cyclopentyloxy-4-methoxyphenylsulfonyl)-5-(3,4-dihydro-2H-quinolin-1yl)5-oxo-pentanoic acid;

3-(3-cyclopentyloxy-4-methoxyphenylsulfonyl)-7-phenylheptanoic acid;

3-(7-methoxy-2-methoxymethyl-3H-benzimidazol-4-yl)sulfonyl-7-phenylheptanoic acid;

3-(7-methoxy-2-cyclopropyl-3H-benzimidazol-4-yl)sulfonyl-7-phenylheptanoic acid;

3-(7-methoxy-2-methoxymethyl-3H-benzimidazol-4-ylsulfonyl)-7-phenylheptanohydroxamic acid;

3-(7-methoxy-2-cyclopropyl-3H-benzimidazol-4-ylsulfonyl)-7-phenylheptanohydroxamic acid;
3-(4-methoxy-3-[trans-3-phenoxy-cyclopentyloxy]phenylsulphonyl)-7-phenylheptanohydroxamic acid;
3-(4-methoxy-3-[trans-3-(pyridin-2-yloxy)-cyclopentyloxy]phenylsulphonyl)-7-phenylheptanohydroxamic acid;
3-(4-methoxy-3-[trans-3-(pyridin-3-yloxy)-cyclopentyloxy]phenylsulphonyl)-7-phenylheptanohydroxamic acid;
3-(4-methoxy-3-[trans-3-(pyridin-4-yloxy)-cyclopentyloxy]phenylsulphonyl)-7-phenylheptanohydroxamic acid;
3-(4-methoxy-3-[cis-3-(pyridin-2-yloxy)-cyclopentyloxy]phenylsulphonyl)-7-phenylheptanohydroxamic acid;
3-(4-methoxy-3-[cis-3-(pyridin-3-yloxy)-cyclopentyloxy]phenylsulphonyl)-7-phenylheptanohydroxamic acid;
3-(3-[N-t-butoxycarbonylpyrrolidin-3-yloxy]-4-methoxyphenylsulphonyl)-7-phenylheptanohydroxamic acid;
3-(4-methoxy-3-[N-phenyl)pyrrolidin-3-yloxy]phenylsulphonyl)-7-phenylheptanohydroxamic acid;
3-(4-methoxy-3-(2-phenyl-ethoxy)phenylsulphonyl)-7-phenylheptanohydroxamic acid;
3-(4-methoxy-3-(4-phenyl-butoxy)phenylsulphonyl)-7-phenylheptanohydroxamic acid;
3-(4-difluoromethoxy-3-[2-phenylethoxy]phenylsulphonyl)-7-phenylheptanohydroxamic acid;
3-(4-methoxy-3-(2-benzyloxyethoxy)phenylsulphonyl)-7-phenyltheptanohydroxamic acid;
3-(4-methoxy-3-(2-phenoxyethoxy)phenylsulphonyl)-7-phenylheptanohydroxamic acid;
3-(5-methoxy-4-[2-(4-methoxyphenyl)ethoxy]pyridin-2-ylsulphonyl)-7-phenylheptanohydroxamic acid;
3-(4-methoxy-3-(2-indanyloxy)phenylsulphonyl)-7-phenylheptanohydroxamic acid;
3-(4-methoxy-3-[2-(pyridin-2-yl)ethoxy]phenylsulphonyl)-7-phenylheptanohydroxamic acid;
3-(4-methoxy-3-[3-(pyridin-4-yl)propyloxy]phenylsulphonyl)-7-phenylheptanohydroxamic acid;
3-(4-methoxy-3-[3-(pyridin-3-yl)propyloxy]phenylsulphonyl)-7-phenylheptanohydroxamic acid;
3-(5-methoxy-4-[2-(pyridin-2yl)ethoxy]pyridin-2-ylsulphonyl)-7-phenylheptanohydroxamic acid;
3-(4-methoxy-3-(2-thien-2-ylethoxy)phenylsulphonyl)-7-phenylheptanohydroxamic acid;
3-(3-{3-(4-chlorophenyl)-1,2,4-oxadiazol-5-ylmethoxy}-4-methoxyphenylsulphonyl)-7-phenylheptanohydroxamic acid;
3-(3-{3-(4-methoxyphenyl)-1,2,4-oxadiazol-5-ylmethoxy}-4-methoxyphenylsulphonyl)-7-phenylheptanohydroxamic acid;
3-(3-[3-(pyridin-2-yl)-1,2,4-oxadiazol-5-ylmethoxy]-4-methoxyphenylsulphonyl)-7-phenylheptanohydroxamic acid;
3-(3-[2-(4-chlorophenyl)-1,3,4-oxadiazol-5-ylmethoxy]-4-methoxyphenylsulphonyl)-7-phenylheptnaohydroxamic acid;

and the corresponding N-oxides, and their prodrugs, pharamceutically acceptable salts, and solvates.

25. A pharmaceutical composition comprising an effective amount to inhibit cyclic AMP phosphodiesterase and/or TNF of a compound according to claim 1 in association with a pharmaceutically acceptable carrier or excipient.

26. A pharmaceutical composition for the treatment of diseases or disorders of the respiratory system comprising an effective amount of a compound according to claim 1 in association with a pharmaceutically acceptable carrier or excipient.

27. A pharmaceutical composition for the treatment of joint inflammation comprising an effective amount of a compound according to claim 1 in association with a pharmaceutically acceptable carrier or excipient.

28. A method for the treatment of diseases or disorders of the respiratory system comprising administering to a patient an effective amount of a compound according to claim 1.

29. A method for the treatment of joint inflammation comprising administering to a patient an effective amount of a compound according to claim 1.

30. A compound of claim 1 in which Ar is a group of formula (i) (where $Q^1$, $Q^2$ and $Q^3$ are each CH, $Z^1$ and $Z^2$ are both oxygen, $R^7$ is methyl, $R^8$ is cyclopentyl and $A^2$ is a direct bond); $A^1$ is a direct bond; n is 2; $R^1$ is hydrogen; $R^2$ is hydrogen; $R^4$ is hydrogen; $R^3$ is $(CH_2)_4Ph$; and Y is CONHOH.

* * * * *